(12) United States Patent
Shih et al.

(10) Patent No.: US 10,357,196 B2
(45) Date of Patent: Jul. 23, 2019

(54) DEPTH MEASUREMENT IN TISSUE USING PIEZOELECTRIC SENSORS HAVING DIFFERENT PROBE SIZES

(71) Applicants: Wan Y. Shih, Bryn Mawr, PA (US); Wei-Heng Shih, Bryn Mawr, PA (US); Xin Xu, Philadelphia, PA (US)

(72) Inventors: Wan Y. Shih, Bryn Mawr, PA (US); Wei-Heng Shih, Bryn Mawr, PA (US); Xin Xu, Philadelphia, PA (US)

(73) Assignee: DREXEL UNIVERSITY, Philadelphia, PA (US)

(*) Notice: Subject to any disclaimer, the term of this patent is extended or adjusted under 35 U.S.C. 154(b) by 270 days.

(21) Appl. No.: 15/109,860

(22) PCT Filed: Jan. 7, 2015

(86) PCT No.: PCT/US2015/010412
§ 371 (c)(1),
(2) Date: Jul. 6, 2016

(87) PCT Pub. No.: WO2015/105827
PCT Pub. Date: Jul. 16, 2015

(65) Prior Publication Data
US 2016/0331300 A1 Nov. 17, 2016

Related U.S. Application Data

(60) Provisional application No. 61/925,203, filed on Jan. 8, 2014.

(51) Int. Cl.
*A61B 5/00* (2006.01)
*A61B 5/107* (2006.01)

(52) U.S. Cl.
CPC ............ *A61B 5/444* (2013.01); *A61B 5/1075* (2013.01); *A61B 2562/0247* (2013.01)

(58) Field of Classification Search
CPC .......... A61B 5/1075; A61B 2562/0247; A61B 5/444
See application file for complete search history.

(56) References Cited

U.S. PATENT DOCUMENTS 7,497,133 B2   3/2009   Shih et al.
2005/0277852 A1   12/2005   Shih et al.
(Continued)

FOREIGN PATENT DOCUMENTS

CN   103263250 A   8/2013
WO   WO2009140660 A2   11/2009

OTHER PUBLICATIONS

V. Egorov and A. P. Sarvazyan, "Mechanical imaging of the breast," Medical Imaging, IEEE Transactions on, vol. 27, pp. 1275-1287, 2008.

(Continued)

*Primary Examiner* — Sean P Dougherty
(74) *Attorney, Agent, or Firm* — Mendelsohn Dunleavy, P.C.

(57) ABSTRACT

An apparatus and method for determining the depth of an object below a surface or the thickness of the dermis. The apparatus and method use a plurality of piezoelectric fingers having probes with differently sized contact areas. A plurality of measurements is taken using each of the probes with differently sized contact areas in order to determine the depth of an object below a surface or the thickness of the dermis.

17 Claims, 23 Drawing Sheets
(13 of 23 Drawing Sheet(s) Filed in Color)

(56) References Cited

U.S. PATENT DOCUMENTS

| | | |
|---|---|---|
| 2007/0106291 A1 | 5/2007 | Thao et al. |
| 2009/0301196 A1 | 12/2009 | Wang et al. |
| 2011/0172565 A1 | 7/2011 | Shih et al. |
| 2012/0053489 A1 | 3/2012 | Shih et al. |

OTHER PUBLICATIONS

V. Egorov, T. Kearney, S. B. Pollak, C. Rohatgi, N. Sarvazyan, S. Airapetian, et al., "Differentiation of benign and malignant breast lesions by mechanical imaging,".

A. Markidou, W. Y. Shih, and W. H. Shih, "Soft-materials elastic and shear moduli measurement using piezoelectric cantilevers," Review of scientific instruments, vol. 76, p. 064302, 2005.

H. O. Yegingil, W. Y. Shih, W. Anjum, A. D. Brooks, and W. H. Shih, "Soft tissue elastic modulus measurement and tumor detection using piezoelectric fingers," in MRS Fall Meeting, 2005.

H. Yegingil, W. Y. Shih, and W. H. Shih, "Probing elastic modulus and depth of bottom supported inclusions in model tissues using piezoelectric cantilevers," Review of scientific instruments, vol. 78, p. 115101, 2007.

S. T. Szewczyk, W. Y. Shih, and W. H. Shih, "Palpationlike soft-material elastic modulus measurement using piezoelectric cantilevers," Review of scientific instruments, vol. 77, p. 044302, 2006.

X. Xu, C. Gifford-Hollingsworth, R. Sensenig, W.-H. Shih, W. Y. Shih, and A. D. Brooks, "Breast Tumor Detection Using Piezoelectric Fingers: First Clinical Report," Journal of the American College of Surgeons, 2013.

A. Samani and D. Plewes, "An inverse problem solution for measuring the elastic modulus of intact ex vivo breast tissue tumours," Physics in medicine and biology, vol. 52, p. 1247, 2007.

A. Samani, J. Zubovits, and D. Plewes, "Elastic moduli of normal and pathological human breast tissues: an inversion-technique-based investigation of 169 samples," Physics in medicine and biology, vol. 52, p. 1565, 2007.

J. Manschot and A. Brakkee, "The measurement and modelling of the mechanical properties of human skin< i> in vivo</i>—II. The model," Journal of Biomechanics, vol. 19, pp. 517-521, 1986.

C. Pailler-Mattei, S. Bec, and H. Zahouani, "< i> In vivo</i> measurements of the elastic mechanical properties of human skin by indentation tests," Medical engineering & physics, vol. 30, pp. 599-606, 2008.

International Search Report and Written Opinion; dated Apr. 20, 2015 for PCT Application No. PCT/US2015/010412.

Xu, X., et al. "A Model Study of 3-Dimensional Localization of Breast Tumors using Piezoelectric Fingers of Different Probe Sizes," Department of Materials Science and Engineering, Drexel University.

H. O. Yegingil, "Breast cancer detection and differentiation using piezoelectric fingers," PhD, Drexel University, 2009.

DEPTH MEASUREMENT IN TISSUE USING PIEZOELECTRIC SENSORS HAVING DIFFERENT PROBE SIZES

RELATED APPLICATION DATA

This application is a 371 continuation of International Patent Application No. PCT/US15/10412, filed on Jan. 7, 2015, which, in turn, claims the benefit of U.S. provisional application No. 61/925,203, filed on Jan. 8, 2014.

BACKGROUND OF THE INVENTION

1. Field of the Invention

The present invention is directed to sensors. In particular the present invention is directed to piezoelectric sensors.

2. Description of the Related Technology

One type of cancer is melanoma. Melanoma is a malignant tumor of melanocytes, which are melanin-producing cells located predominately in the skin. Melanoma is believed by many clinicians to be one of the most aggressive types of malignancies. Although melanoma accounts for only 4 percent of all skin cancers, it is responsible for 80 percent of skin cancer deaths, and its incidence and mortality have increased steadily over the past three decades. It is estimated that approximately 76,690 new cases of invasive melanoma will be diagnosed in the United States in 2013, and about 9,480 people will die of the disease [1]. The earliest stage of melanoma grows radially within the epidermis, and becomes increasingly lethal as it advances deeper into the skin. Melanoma thickness (illustrated in FIG. 1), or Breslow Thickness (BT), is the most important histopathological factor for staging and is closely related to survival rate [2]. The five-year survival rate is 95% if the tumor thickness is less than 1 mm, while the survival rate is reduced to 50% when the tumor thickness is greater than 4 mm [3, 4].

BT is commonly measured by removing a portion of the lesion by a shave or punch biopsy and then histologically examining the sample. This method, when completed by experienced dermatologists, has been shown to underestimate the BT about 12% to 20% of the time. Complete excision of the lesion is the most accurate method of measuring BT, but this is often impossible due to the lesion covering too large a surface area or being in an aesthetically sensitive location [5]. Moreover, 80% of malpractice claims relating to melanoma cite incomplete biopsy specimens as a contributing factor in disease progression [6].

Another issue with melanoma surgery is that the parameters for excision depth and surgical margins are highly inconsistent among dermatologists in terms of completely eliminating the lesion [7, 8]. For example, if the melanoma thickness is <1 mm (<2 mm) then a lateral area of 1 cm (2 cm) is removed. As a result, a tedious and time-consuming process called Mohs surgery is commonly used to determine if the entirety of a malignant lesion has been removed. During this procedure, a surgeon serially removes and histologically examines sections of the lesion until the margins are clear of malignant cells. Therefore, a tool that can conclusively and non-invasively measure the thickness of skin lesions in vivo would be invaluable for improving the accuracy of the assessment of melanoma staging, and for determining the margins for surgical removal before the operation.

Another type of cancer is breast cancer, which has been the cancer type with one of the highest fatality rates for women over the past several decades. It is the most common non-skin malignancy diagnosed in women. In the United States, there will be 232,340 invasive breast cancer cases and 64,640 carcinomas in situ diagnosed in 2013 [9]. It is estimated that 500,000 women in the world will die from breast cancer each year [10].

Accurate preoperative assessment of breast tumor locations and sizes in three dimensions (3D) are important for both biopsies and surgeries [11]. Clinical breast examination (CBE), ultrasound, mammography, and magnetic resonance imaging (MRI) are the main currently used breast tumor detection and localization methodologies [12, 13]. CBE cannot provide a quantitative value of the tumor size and has difficulty detecting lesions with indistinct borders, lesions in large breasts, and non-palpable lesions [14, 15]. Mammography, MRI, and ultrasound project a 3D tumor on a two dimensional (2D) plane. Although mammography takes two pictures, one viewed from top to bottom and the other from a 45° angle, it is still difficult to pinpoint the actual location and extent of the tumor using this method. Compression of the breast can also lead to distortion of the location and extent of the tumor. Variations in the distance between the lesion and mammogram film and vague lesion boundaries can introduce error to the measurements [14]. Moreover, standard imaging methods do not always capture the maximum tumor extent [16]. In addition, patients are in a different position during typical mammography imaging than the supine position that is typically used during surgery. Such differences can further distort the 3D localization of the tumor.

While ultrasound is widely available and does not require compression of the breast it frequently underestimates the tumor size [17-19]. This may lead to incomplete excision in a lumpectomy [11]. Ultrasound also does not detect all types of tumors.

MRI requires compression of the tumor for accurate detection. A recent study indicated that MRI also frequently underestimates the size of breast lesions especially those of ductal carcinoma in situ (DCIS) [20]. The discordance between the tumor size on MRI and the pathological size may contribute to the number of re-excisions required for patients that undergo lumpectomy procedures.

A technique that can detect not only the presence but also the 3D location of the tumor, and particularly the depth location of the tumor, will provide more accurate biopsies and surgeries. Precise measurement of tumor sizes in 3D is also important to monitor the response to chemotherapy for breast tumors. It is well known that breast tumors are stiffer than the surrounding normal tissue. This property allows breast tumors to be detected by contrasting tissue stiffness, and can allow 3D mechanical imaging and sizing of breast tumors.

SureTouch™, a breast tumor imaging system, developed by Egorov et al., reconstructs the 3D tumor image from a series of 2D pressure distribution maps based on the assumption that a higher compression force leads to a better representation of the deeper structures in a 2D pressure map [21-23]. However, the accuracy of the SureTouch™ in determining the depth profile of breast cancer tumors has not been reported [23]. The smallest size of inclusions detected by this method in a breast model was 5 mm [22].

Another approach employs a tactile sensation imaging system (TSIS). This approach first generates tactile sensation imaging data and correlates this data using finite element simulations, followed by applying an artificial neural network to extract the size, depth, and Young's modulus of the tumor [24-26]. The smallest size of inclusions detected by this method in the models was 2 mm. This method was based on the assumption that all the tumors were spherical in shape. This was not an accurate assumption since most of the breast tumors had irregular or asymmetric shapes [27, 28].

A piezoelectric finger (PEF) is a type of sensor that can measure tissue elastic modulus (E) in vivo by contacting the PEF with the tissue [29-32]. A tumor could be directly detected by contrasting the stiffness of the tumor, as indicated by the measured tissue elastic modulus, with the stiffness of surrounding normal tissue. What makes PEF different from the tactile imaging technologies is that PEF measures the elastic modulus of the tissue but not the pressure distribution. This distinction makes PEF measurements insensitive to the pressure applied to the device [33] during the data collection process, which in turn makes the measurement less dependent on the operator of the device. Also, this method does not require an algorithm to remove the background pressure profile [22, 23] as do some other tactile imaging methods.

The fabrication and characterization of PEFs can be found in references [29-31]. PEFs have been used to detect breast cancer by contrasting the stiffness of the lesion with that of the surrounding tissue without the need to employ inversion simulations or pattern recognition software (see WO 2009/140660, the disclosure of which is hereby incorporated herein by reference in its entirety). PEFs are also described in U.S. Pat. No. 7,497,133, the disclosure of which is also hereby incorporated herein by reference.

In previous in vivo studies, PEFs have been tested on 40 patients and these tests have demonstrated that PEFs are capable of detecting most types of breast tumors in vivo, including at least fibroadenomas, cysts, invasive carcinomas and ductal carcinomas in situ. The overall sensitivity of the PEF test was 87%. In women 40 years and younger, the overall sensitivity was 100%. The smallest tumor detected by a PEF was 2×5 mm [33]. Model tissue studies have also shown that the detectable depth obtained by using a PEF was twice that of the probe size of the PEF [31]. In other words, with a larger probe size a PEF can assess the elastic response of tissue at greater depths from the tissue surface.

SUMMARY OF THE INVENTION

An aspect of the present invention may be a device comprising a plurality of piezoelectric fingers wherein each piezoelectric finger comprises a first piezoelectric layer; a second piezoelectric layer; a non-piezoelectric layer, a portion of which is located between the first and second piezoelectric layers; and a probe having a contact area and being located at a distal end of the non-piezoelectric layer or a distal end of one said piezoelectric layer; and wherein at least one probe has a contact area with a different size than a size of a contact area of at least one other said probe.

Another aspect of the present invention may be a method of determining a depth of an object comprising steps of: (a) taking a first measurement while contacting a surface with a first contact area of a first piezoelectric finger; (b) taking a second measurement while contacting the surface with a second contact area of a second piezoelectric finger, wherein the second contact area has a different size than a size of the first contact area; and (c) determining the depth of an object beneath the surface using the first and second measurements.

Still yet another aspect of the present invention may be a method of determining a thickness of dermis comprising steps of: a) taking a first measurement while contacting a surface with a first contact area of a first piezoelectric finger; (b) taking a second measurement while contacting the surface with a second contact area of a second piezoelectric finger, wherein the second contact area has a different size than a size of the first contact area; and (c) determining the thickness of the dermis beneath the surface using the first and second measurements.

BRIEF DESCRIPTION OF THE DRAWINGS

The application file contains at least one drawing executed in color. Copies of this patent application publication with color drawings will be provided by the Office upon request and payment of the necessary fee.

DETAILED DESCRIPTION OF THE PREFERRED EMBODIMENT(S)

For illustrative purposes, the principles of the present disclosure are described by referencing various exemplary embodiments. Although certain embodiments are specifically described herein, one of ordinary skill in the art will readily recognize that the same principles are equally applicable to, and can be employed in other systems and methods.

Before explaining the disclosed embodiments of the present disclosure in detail, it is to be understood that the disclosure is not limited in its application to the details of any particular embodiment shown. Additionally, the terminology used herein is for the purpose of description and not of limitation. Furthermore, although certain methods are described with reference to steps that are presented herein in a certain order, in many instances, these steps may be performed in any order as may be appreciated by one skilled in the art; the novel methods are therefore not limited to the particular arrangement of steps disclosed herein.

It is be noted that as used herein and in the appended claims, the singular forms "a", "an", and "the" include plural references unless the context clearly dictates otherwise. Furthermore, the terms "a" (or "an"), "one or more" and "at least one" can be used interchangeably herein. The terms "comprising", "including", "having" and "constructed from" can also be used interchangeably.

Figure 1:
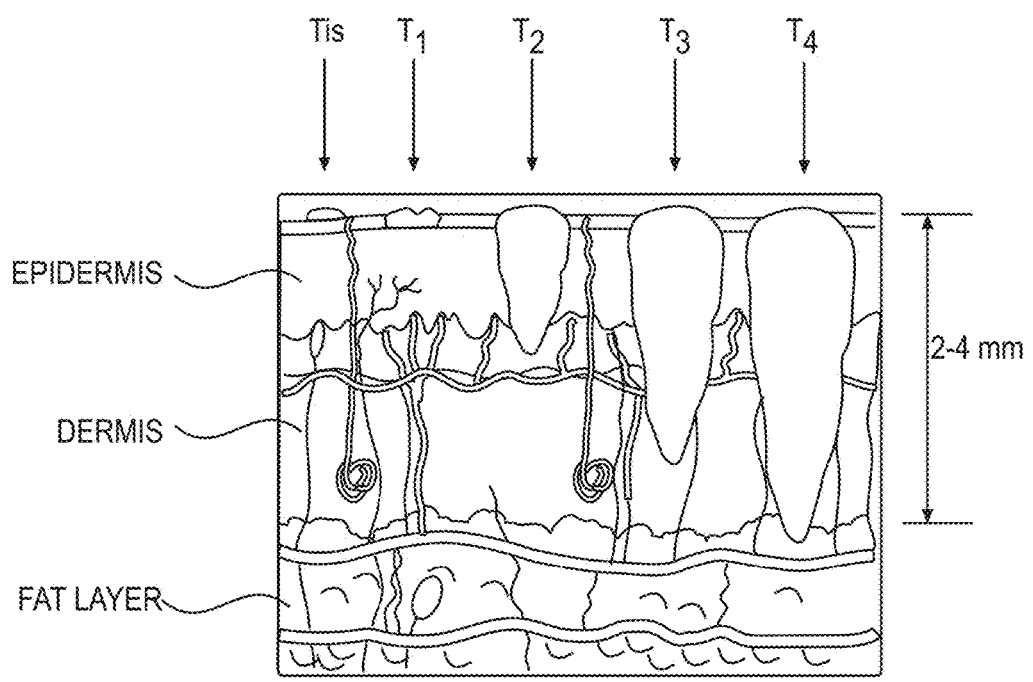
FIG. 1 is a diagram showing the depths of skin cancer tumors in stages T1-T4.
Figure 2A:
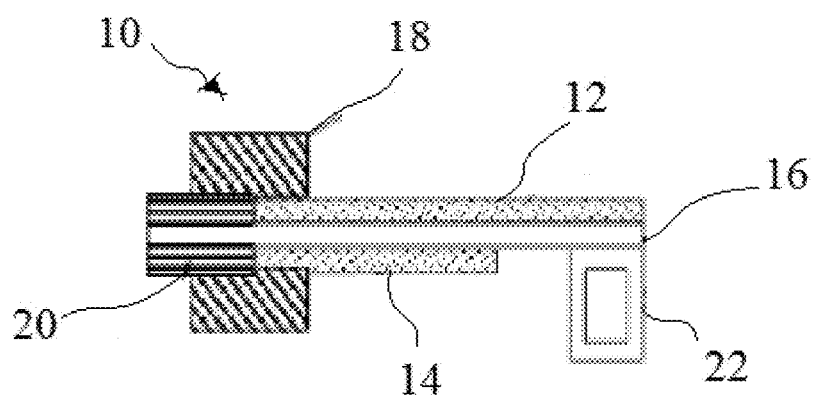
FIG. 2A is a diagram showing a PEF in accordance with an embodiment of the present invention.

Referring now to FIG. 2A, a diagram of a piezoelectric finger (PEF) 10 in accordance with embodiments of the present invention is shown. PEF 10 is a piezoelectric cantilever with two piezoelectric layers, a top piezoelectric layer 12 and a bottom piezoelectric layer 14. These top and bottom piezoelectric layers 12, 14 may be made of lead zirconate titanate (PZT) (T105-H4E-602, Piezo Systems Inc.), or some other suitable piezoelectric material. Other materials suitable for the top and bottom piezoelectric layers 12, 14 include, for example, lead magnesium niobate, lead titanate solid solution (PMN-PT), or any other piezoelectrics material. The top piezoelectric layer 12 and the bottom piezoelectric layer 14 may have a non-piezoelectric layer 16 located between them. The non-piezoelectric layer 16 may be a stainless steel layer (Alfa Aesar), or some other suitable non-piezoelectric material. The PEF 10 may further comprise a clamp 18, a spacer 20 and probe 22. The probe 22 may be attached to a distal end of the non-piezoelectric layer 14.

Figure 2B:
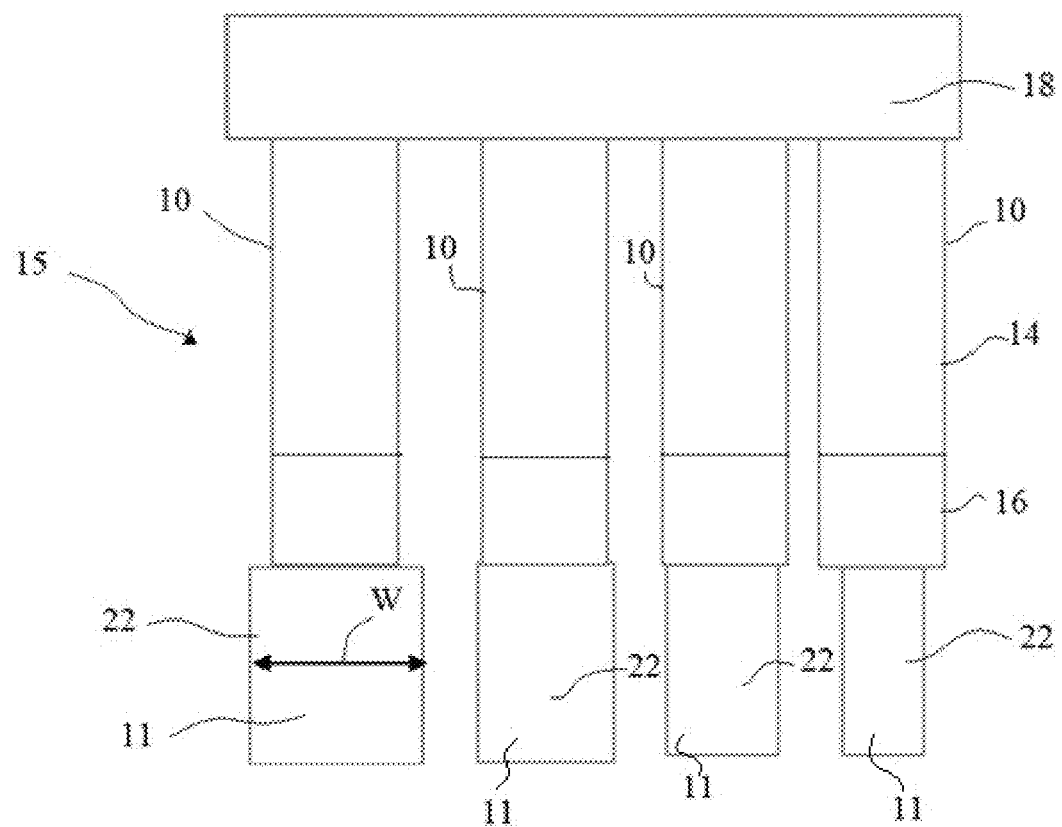
FIG. 2B shows a schematic showing a bottom-up view of an array of PEFs having different sizes of contact areas of probes.

FIG. 2B shows an array 15 of PEFs 10 having probes 22 of different sizes. In the embodiment of FIG. 2B the probes 22 have different widths (W) and the same lengths (L) (not shown), which results in each probe 22 having a contact area 11 of a different size.

As used herein "probe size" generally refers to the contact area 11 of the probe unless stated otherwise. The probe 22 may be rectangular, cylindrical or have some other geometry. When discussed herein, references to the width of a probe 22, may generally refer to a dimension taken across a contact area 11 of a rectangular or other shaped probe 22, references to the radius of a probe 22, or diameter of a probe 22 generally refers to a dimension taken across a contact area 11 a cylindrical probe 22. However, when either the radius or the width are generally discussed herein, the results of changing either radius or width has on the contact area 11 are generally similar, unless specifically stated otherwise. The contact area 11 is that portion of the probe 22 that comes into contact with a surface when in use.

In discussing the methods below, it should be understood that the methods can be performed using a plurality of separate PEFs 10 each having probes 22 having contact areas 11 of different sizes, or using an array 15 of a plurality of PEFS 10 having probes 22 with contact areas 11 of different sizes. In general, the probes 22 are used in a method determining the depth of an object below a surface. Preferred contact areas 11 of the probes 22 are in the range of 0.1 to 50 mm$^2$ for detection of melanomas and 10 to 100 mm$^2$ for detection of various forms of breast cancer.

The PEF 10 can be employed to measure the elastic modulus of a soft material or tissue using an "all electric" measurement method. In one such method, a direct current (DC) voltage is applied to the top piezoelectric layer 12 of a PEF 10 thereby causing the PEF 10 to bend due to the converse piezoelectric effect. The bending of the PEF 10 generates an induced piezoelectric voltage in the sensing bottom piezoelectric layer 14 [32]. Pressure is then applied to a surface such as the surface of tissue via the contact area 11 of probe 22 by the operator of the device. The resistance of the tissue to the applied pressure will affect the degree of bending of the sensing bottom piezoelectric layer 14, with stiffer tissue having a greater effect on the degree of bending than more malleable tissue. This effect on the degree of bending will, in turn, influence the electrical voltage output of the sensing bottom piezoelectric layer 14.

An aspect of the present invention is that it employs an array 15 of PEFs 10 each with a probe 22 having a contact area 11 of a different size to examine the tissue. The obtained results can be used to deduce the tissue elastic modulus profile in the thickness direction. PEFs 10 having contact areas 11 of different size can be employed to contrast tumor elastic modulus at different depths within the tissue with the elastic modulus of the surrounding tissue. For example, a 3D melanoma thickness map can be obtained by measuring the elastic modulus of the tumor and contrasting the measured elastic modulus with the elastic modulus of the surrounding tissue using an array 15 of PEFs 10 each having a contact area 11 of a different size.

Figure 3A:
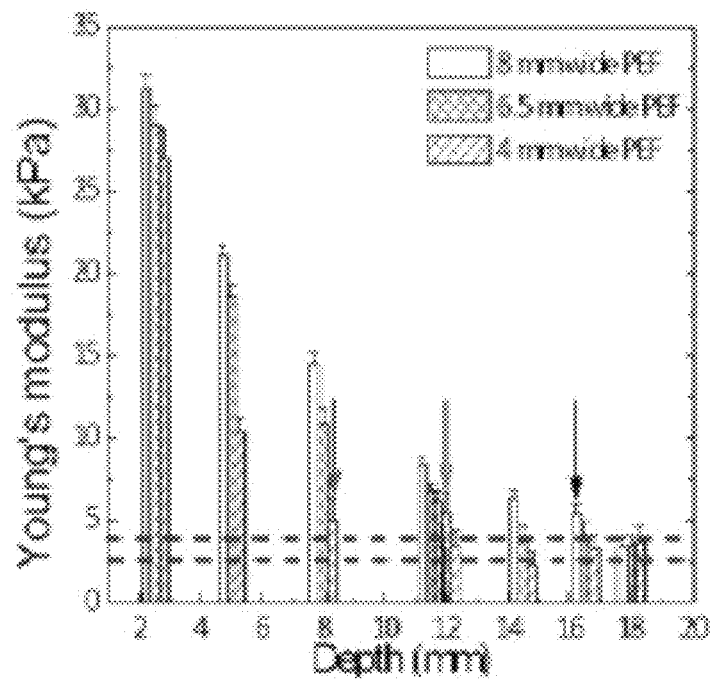
FIG. 3A is a graph of Young's modulus vs. depth.

One embodiment of the invention is directed to a method of determining a depth profile of a breast including one or more tumors. As a starting point, a two-dimensional map showing the location of one or more tumors can be made using prior art techniques. Typically, in the case of tumors of the breast there is a layer of softer tissue located atop a tumor of harder tissue. Each probe 22 is designed with a specific contact area 11 for the purpose of investigating a characteristic depth sensitivity that results from the size of contact area 11, as shown in FIG. 3A. Specifically, FIG. 3A shows graphs of Young's modulus vs. depth for probes 22 having three different contact areas 11, as indicated by the different widths of the PEF given in the figure (the lengths of the contact areas are held constant such that the differences in width correlate with differences in contact area).

Figure 3B:
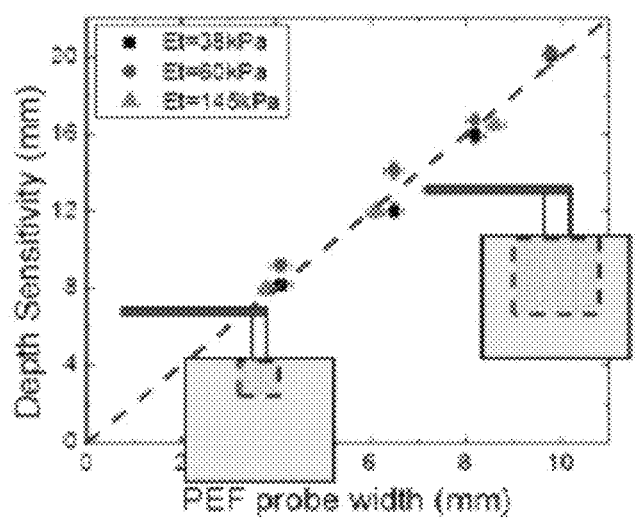
FIG. 3B is a graph of depth sensitivity vs. PEF probe width.

In FIG. 3B the depth sensitivity vs. the width of the contact area 11 of PEF 10 is shown. As can be seen from FIG. 3B, a key feature of the present invention is that each size of contact area 11 correlates with a particular depth sensitivity such that measurements using PEF's 10 with different contact areas 11 can be employed to provide a depth profile of the elastic modulus of the tissue. In this manner, the depth of both the top and bottom of a tumor can be determined using iterative finite element analysis. This allows the determination of important information for diagnosis and treatment planning since, as discussed above, tumor thickness (depth) correlates with survival rates and influences treatment planning both as to the type of treatment(s) selected and as to the size of the excision required for surgical treatment.

In this method, plural PEF's 10 each having a different skin surface contact area 11 are employed to take measurements at the same location on the skin. From these measurements, the elastic modulus E is calculated.

Figure 4:
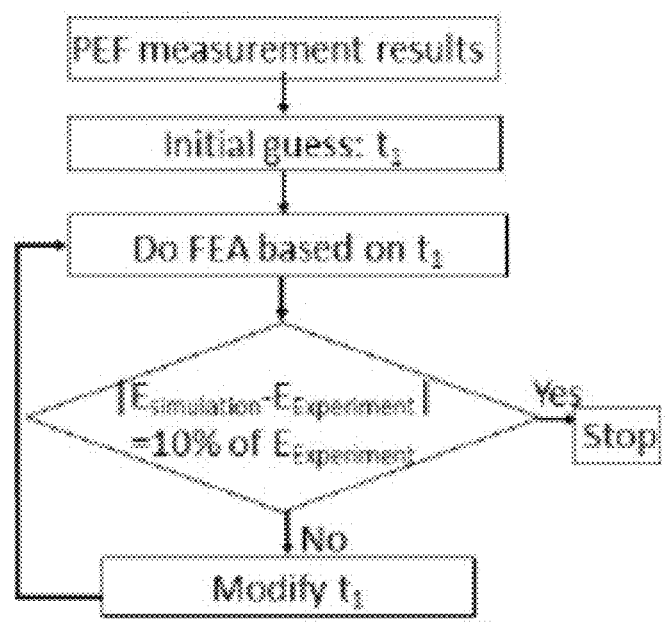
FIG. 4 is a flow chart showing the determination of tumor depth using iterative finite element analysis (FEA).
Figure 5:
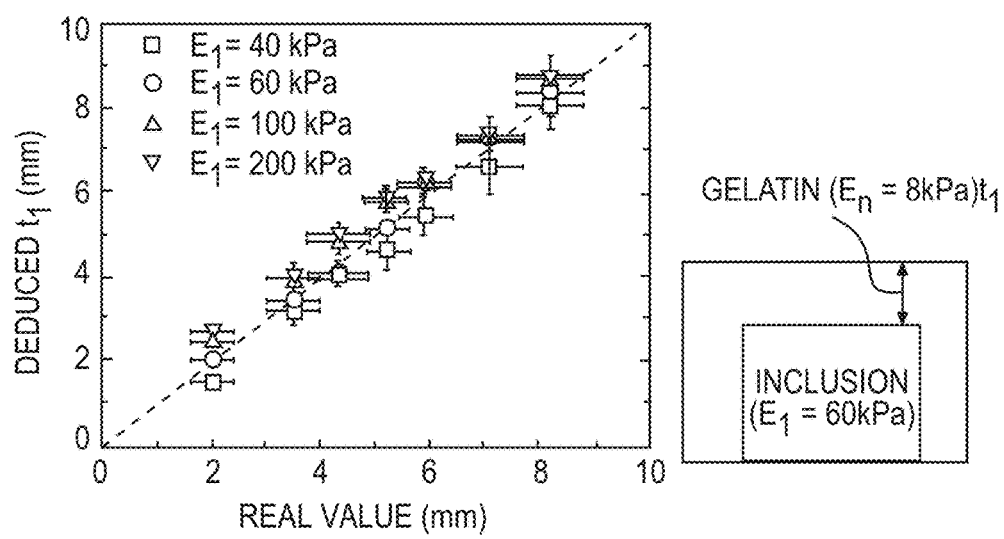
FIG. 5 is a graph showing the determination of tumor depth using iterative FEA.

The experimental results determining the elastic modulus E are coupled with iterative finite element analysis as shown in FIG. 4 to find a best fit for the measured data, eventually solving for the thickness $t_1$ of the soft tissue layer above the stiffer tumor. The results are shown in FIG. 5. A goal of $E_{Simulation} - E_{Experiment} = 10\%$ of $E_{Experiment}$ can be set as a stopping point for the iterative process. This provides a reasonable approximation of the depth to the top of the tumor with an acceptable amount of error.

The present invention thus provides 3D tumor location using an array 15 of PEFs 10 each with a probe 22 having a contact area 11 of a different size in order to determine not only the lateral location but also the depth of a tumor in tissue such as breast tissue. Coupling such multiple PEF measurements with a simple spring model allows determination of the 3D location of suspended inclusions such as tumors in tissue.

The finite element analysis, however, is not applicable for suspended inclusions or tumors which are suspended over a third layer of tissue that is softer than the tumor. In such cases, a spring model can be applied to determine both the depth to the top of the tumor and the depth to the bottom of the tumor. The thickness of the tumor can then be determined by subtracting the depth to the top of the tumor from the depth to the bottom of the tumor. It has been shown that using the elastic modulus measurements from two PEFs 10 each with a different sized contact area 11 of probe 22 a two-spring model can be used to determine the depth of a bottom-supported inclusion in model breast tissue [31].

Figure 6:
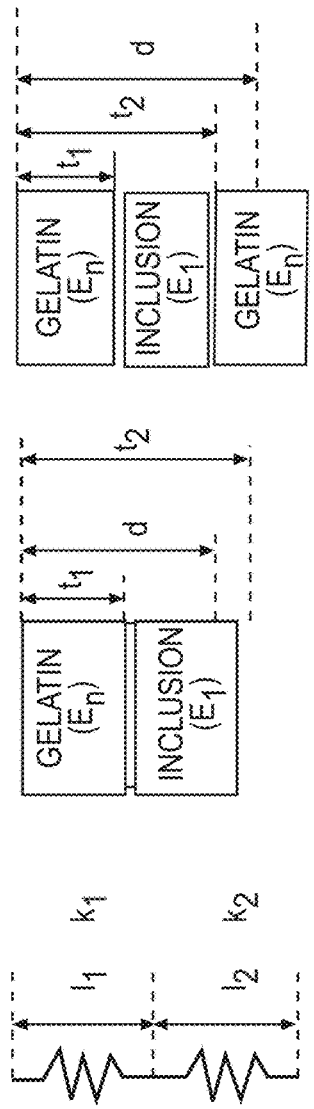
FIG. 6 is a diagram illustrating spring model theory.
Figure 7:
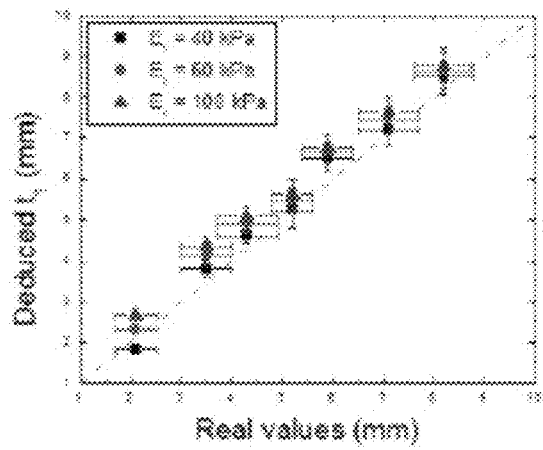
FIG. 7 is a graph depicting deduced tumor depth using the spring model versus the real values.

The formulae for application of the spring model theory are given in FIG. 6. The depth sensitivity of each PEF 10 is a known constant that is determined prior to taking measurements and is a function of the contact area 11 between the PEF 10 and a surface, such as the skin, as shown in FIGS. 3A and 3B. For each measurement, $E_n$ is determined from the measurement using known techniques. The data for $E_n$ is then fit to the formula for the spring model and the thickness t is determined. Since $E_t$ is much larger than $E_n$, the determined thickness t is not sensitive to $E_t$ and thus this portion of the formula can be ignored. The results given in FIGS. 7-9 demonstrate that the determined thicknesses correlate well with actual thicknesses.

E increases as a function of the size of the probe 22 moving toward the bottom of a tumor. At the bottom of the tumor E decreases as a function of the size of the probe 22 indicating that the third, supporting layer of soft tissue has been reached. Thus, this demonstrates that the tumor depth can be deduced quite accurately using the spring model.

Another embodiment of the present invention is directed to a method of determining the thickness of the dermis. In this case, there is a relatively harder dermis layer located atop a relatively softer hypodermis layer. For this situation, the spring model does not work and thus finite element analysis is applied to determine the thickness of the dermis, as shown in FIGS. 10A-10B and FIGS. 11A-11B.

Figure 15:
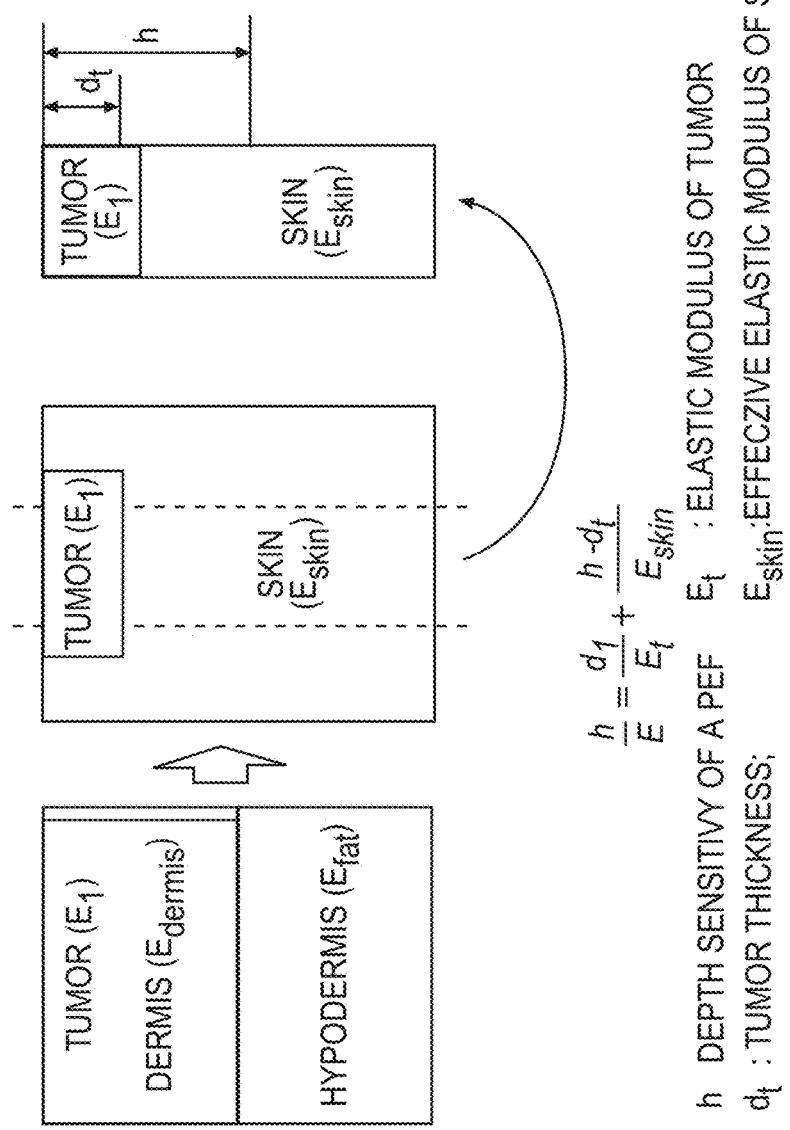
FIG. 15 is a diagram depicting the determination of tumor thickness using spring model theory.
Figure 16A:
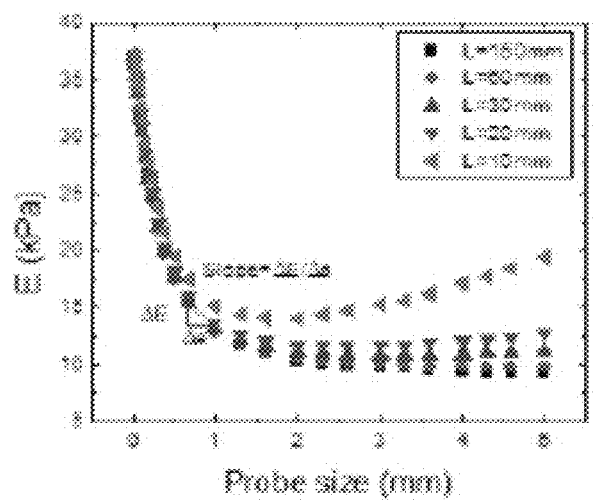
FIG. 16A is a graph depicting E (kPa) v. probe size when excluding the data affected by a substrate
Figure 16B:
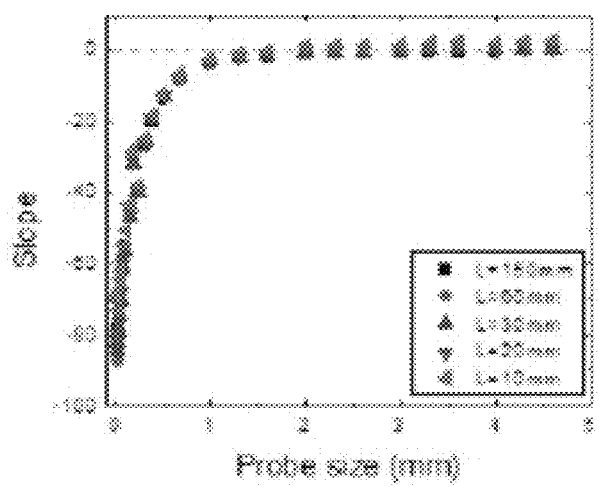
FIG. 16B is a graph depicting slope v. probe contact area size.
Figure 17A:
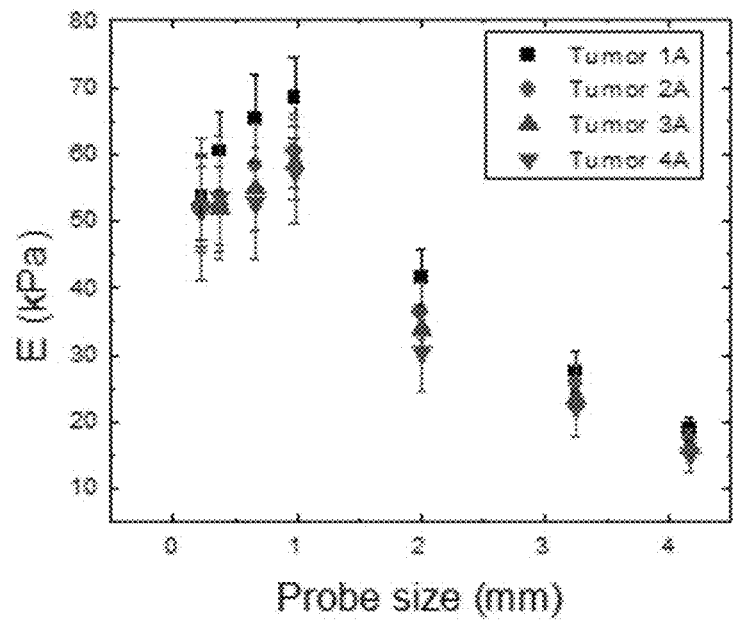
FIG. 17A is graph showing measured elastic modulus E (kPa) using PEFs with different probe contact area sizes.
Figure 17B:
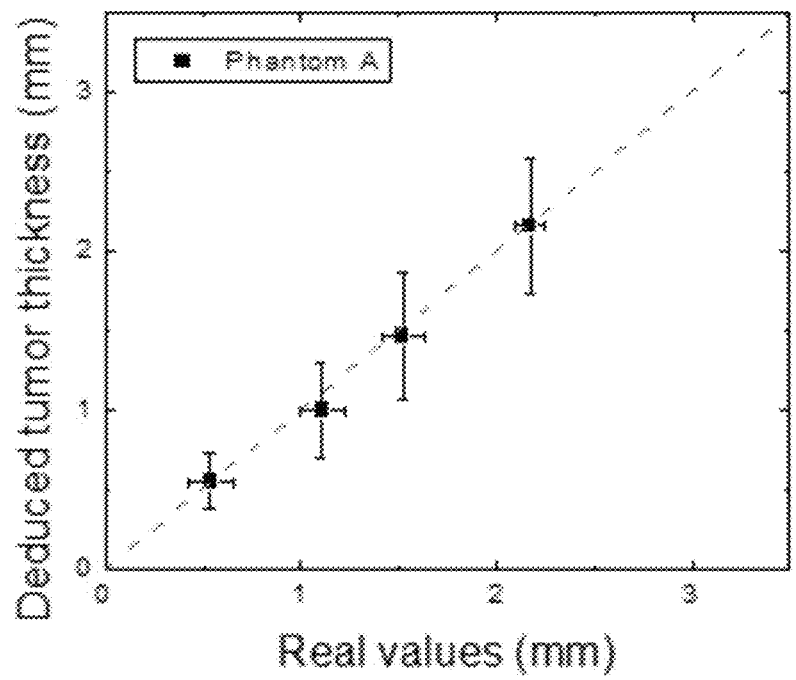
FIG. 17B shows deduced dermis thickness versus the real values.
Figure 17C:
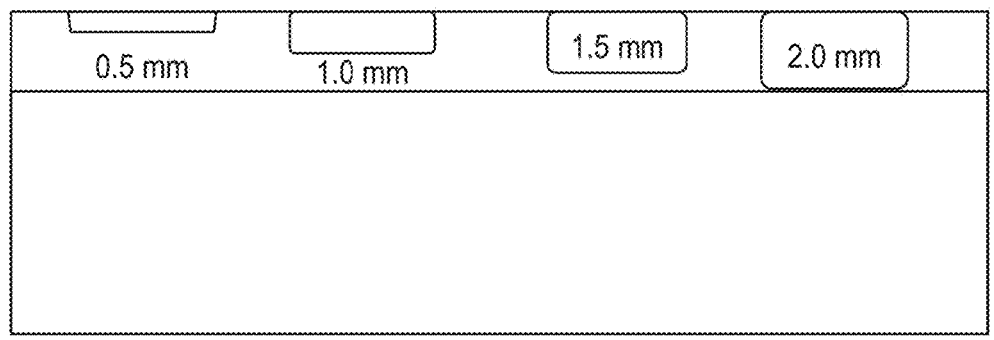
FIG. 17C shows dermis thickness.
Figure 18A:
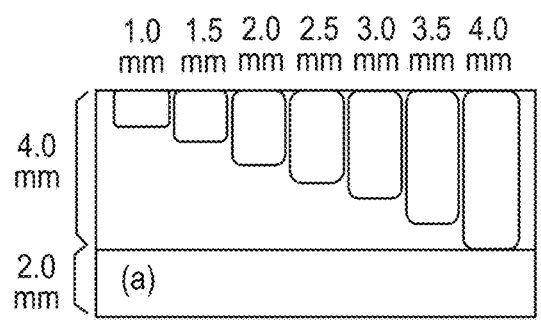
FIG. 18A is a schematic of a phantom sample.
Figure 18B:
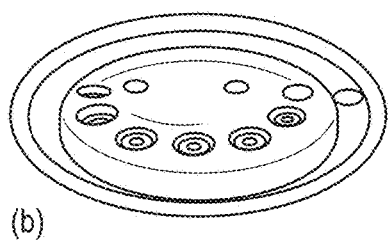
FIG. 18B is a view of a skin sample.
Figure 18C:
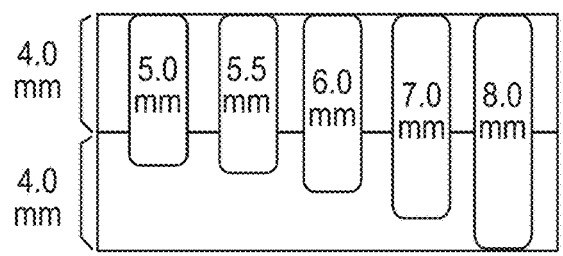
FIG. 18C is a schematic of a phantom sample.
Figure 18D:
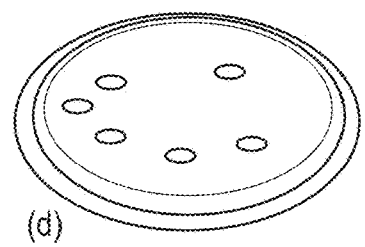
FIG. 18D is a view of a skin sample.

It has been found that the relatively thin epidermis can be ignored in this determination while still producing results of acceptable accuracy, as shown for example in FIGS. 12A-12B, 13A-13B and 14A-14B. The slope of the elastic modulus plot can be used to exclude data influenced by the substrate under the skin phantom that was employed for the testing, as shown in FIGS. 15A and 15B.

Determination of the thickness of the dermis or dermal layer can be important for diagnosis of skin cancer since accurate knowledge of the thickness of the dermal layer can be used to assess the risk of metastasis by comparing the thickness of the dermal layer to a determined thickness of a skin cancer, as shown in FIGS. 16 and 17A-17C. This is because skin cancer typically becomes metastatic once it extends beyond the dermis into the hypodermis.

In this method, a lateral tumor location map is used to identify two measurement locations, one with normal tissue and one directly atop a skin cancer lesion. Measurements are taken using an array 15 of PEFs 10 having probes 22 with different sized contact areas 11 that are contacted with the normal tissue and the elastic modulus for each PEF measurement is determined. The same array 15 of PEFs 10 is then used to take elastic modulus measurements at the location of the skin cancer lesion and the elastic modulus for each measurement is determined. The elastic moduli determinations for each PEF 10 are compared and if the ratio is not close to 1, this indicates the presence of a cancer lesion. When the ratio approaches 1 this indicates that the bottom of the lesion has been passed and normal tissue is being detected. Since the depth sensitivity of each PEF 10 is known, the depth of the lesion can be determined using the known depth sensitivity of each PEF 10.

Once the depth of the lesion is determined, the depth can be compared to the determined thickness of the dermis to estimate the risk factor associated with the skin cancer lesion since lesions approaching or exceeding the thickness of the dermis represent a more significant risk of metastasizing.

Now turning to an application of the PEF 10 in treating breast cancer. It has been shown [30, 32] that the induced voltage is proportional to the tip displacement, d, of the PEF 10. Therefore, the induced voltage can be used to represent the displacement d [30, 32]. As a result, the elastic modulus, E, of the tissue is deduced as:

$$E = \frac{1}{2}\left(\frac{\pi}{A}\right)^{1/2}(1-v^2)\frac{K(V_{in,0} - V_{in})}{V_{in}} \quad [32] \qquad (1)$$

where $V_{in,0}$ and $V_{in}$ are the induced voltages without contact with the tissue and with contact with the tissue, respectively, v is the Poisson's Ratio of the tissue, A is the contact area 11 defined by the stainless steel loop at the tip of the PEF, and K is the effective spring constant of the PEF.

PEFs 10 having probes 22 with contact areas 11 of different sizes were used to measure the elastic modulus over the center of the inclusion in breast models in order to assess the depth profile of the inclusion. The widths of the contact areas 11 of the probes 22 of the PEFs 10 were 4.1±0.2, 6.5±0.2, 8.2±0.2, and 9.8±0.3 mm, respectively. The contact area 11 of the probes 22 is preferably between 10 mm² to 100 mm². The maximum depth that the PEFs 10 used in this experiment could measure was about 20 mm. The dimensions of PEFs 10 used in the experiment are shown below in Table 1.

| PEF cantilever | Width (mm) | Length of upper piezoelectric layer(mm) | Length of upper piezoelectric layer(mm) | contact area (mm²) |
|---|---|---|---|---|
| A | 4.1 ± 0.2 | 22.3 ± 0.3 | 10.1 ± 0.3 | 16 ± 2 |
| B | 6.5 ± 0.2 | 22.6 ± 0.4 | 10.5 ± 0.3 | 42 ± 3 |
| C | 8.2 ± 0.2 | 22.1 ± 0.4 | 10.3 ± 0.4 | 67 ± 4 |
| D | 9.8 ± 0.3 | 22.4 ± 0.4 | 10.6 ± 0.3 | 96 ± 6 |

Breast Model and Measurement Procedures

Gelatin models with suspended clay inclusions were built to mimic a breast with lumps. The clays (Modeling Clay, Crayola, Easton, Pa.), were made into cuboid shapes that were 15 mm in length, 15 mm in width, and having suspended inclusions at different heights (5-15 mm). The elastic modulus of the clay was 60 kPa, and thus was within the range of the elastic modulus of excised breast tumors (30-72 kPa) measured by a PEF 10 in ex vivo breast tumor study [34]. Gelatin powders (Beef gelatin powder, Now Foods, Bloomingdale, Ill.) were mixed with water at 80° C. at a concentration of 0.12 g/ml, which was chosen so that the elastic modulus of the gelatin was about 10 kPa. These choices were consistent with the elastic moduli of both normal breast tissue and breast tumors that have been reported in the literature, which were 3-28 kPa and 11-106 kPa, respectively [35-40]. The gelatin solution was poured into a 35 cm×23 cm×20 cm container and put into a refrigerator for 10 minutes to solidify. Subsequently the clay inclusions were placed on top of the gelatin layer. Afterward, another gelatin solution of the same concentration was poured into the container to enclose the clays inclusions in the gelatin. When the gelatin was solidified, each clay inclusion was suspended in the gelatin matrix. The total height of the gelatin matrix was 34 mm.

Four PEFs 10 with probes 22 having contact areas 11 of different sizes as given in Table 1 above, were used to measure the elastic moduli of the entire gelatin model with inclusions. Five repeated measurements were taken on the same location by each PEF 10, and they were averaged. Since the detectable depths of each of the PEFs 10 were different due to their different sized contact areas 11, distinct E values were obtained using the PEFs 10 on the same location. After the PEF measurements, the depth profile of the tumor, including the distance from the gelatin surface to the top of the tumor ($d_1$) and the distance from the gelatin surface to the bottom of the tumor ($d_2$), were measured using a caliper for comparative use.

Lateral Inclusion Size Determination

Figure 27:
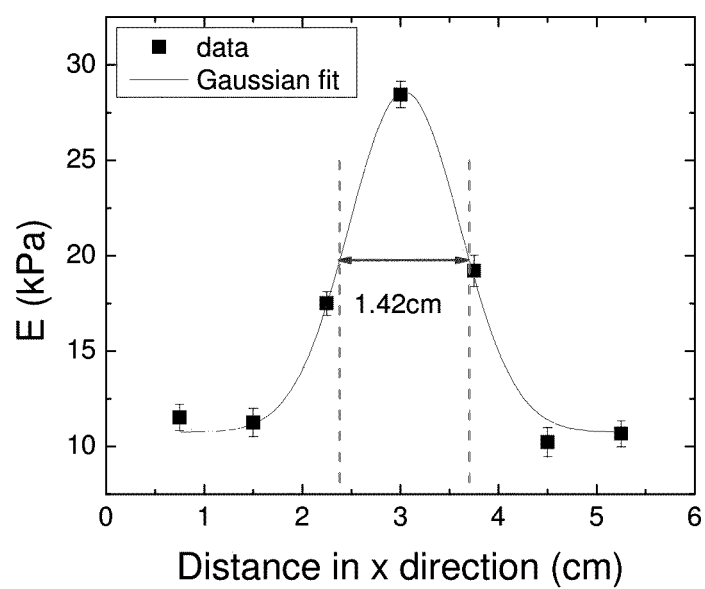
FIG. 27 is a graph of E (kPa) v. distance in the X direction.

To determine the inclusion size in the lateral direction, the elastic modulus along that axis was plotted versus the perpendicular axis. As an example, the elastic modulus versus x at y=3.0 cm is shown by the solid squares in FIG. 27. The data was then fitted to a Gaussian function (solid line). The size of the inclusion at y=3.0 cm was then taken as the width (x=3.80−2.38=1.42 cm) of the half height of the Gaussian function. Similarly, the size of the tumor in the y direction at a particular value of x could also be obtained.

Spring Model Theory

When two springs are connected in series, the overall spring constant k can be calculated using the following equation:

$$\frac{l_1+l_2}{k} = \frac{l_1}{k_1} + \frac{l_2}{k_2} \quad (2)$$

where $l_1$ and $l_2$ are the length of the springs, respectively; and $k_1$ and $k_2$ are the spring constants of the springs, respectively.

When the distance from the gelatin surface to the bottom of the inclusion ($d_1$) is larger than the depth sensitivity of a single PEF (h), the gelatin underneath the inclusion is beyond the detection range of the PEF 10. Therefore, the effect of the gelatin underneath the inclusion is negligible. The gelatin on the top of the inclusion and the inclusion itself can be modeled as two springs in series, and, as a result, the effective elastic modulus E measured by a single PEF 10, can be expressed as:

$$\frac{h}{E} = \frac{d_1}{E_n} + \frac{h-d_1}{E_t} \quad (3)$$

where h is the depth sensitivity of a single PEF 10; $d_1$ is the distance from the surface of the gelatin to the top of the inclusion; and $E_n$ and $E_t$ are the elastic moduli of the gelatin and inclusion, respectively.

When the depth sensitivity of a single PEF 10 is larger than $d_2$, the gelatin underneath the inclusion should be taken into account. Therefore, this situation can be modeled as three springs in series. Then the effective elastic modulus E measured by a single PEF 10, can be expressed as:

$$\frac{h}{E} = \frac{d_1}{E_n} + \frac{d_3-d_1}{E_t} + \frac{h-d_2}{E_r} = \frac{h-(d_2-d_1)}{E_n} + \frac{d_s-d_1}{E_t} \quad (4)$$

where h is the depth sensitivity of a single PEF 10; $d_1$ is the distance from the surface of the gelatin to the top of the inclusion; $d_2$ is the distance from the surface of the gelatin to the bottom of the inclusion; $d_2-d_1$ is the height of the inclusion; and $E_n$ and $E_t$ are the elastic moduli of the gelatin and inclusion, respectively.

The elastic modulus of gelatin ($E_n$) can be obtained by using the PEF 10 on a pure gelatin area, while the elastic modulus of inclusion ($E_t$) could not be measured directly, since the inclusion was embedded in the sample. A previous ex vivo breast tumor study has shown that the elastic moduli of excised breast tumors were in the range of 30 to 72 kPa [34]. Therefore, by using $E_t$=30-72 kpa, the depth profile of the inclusion ($d_1$ and $d_2$) could be obtained. In the study, certain $E_t$ values (i.e. $E_t$=30, 40, 50, 60, and 70 kPa) were employed in Equations (2) and (3) to solve for $d_1$ and $d_2$, and the resultant values were averaged. Extreme $E_t$ values (i.e. $E_t$=100 and 200 kPa) were also used to see how the assumption of $E_t$ affected the estimated d values.

Skin Tumor Phantoms

In this study, the skin layer was mechanically approximated as a homogeneous layer due to the thinness of the epidermis (~0.1 mm thick) as compared to the dermis (2-3 mm thick). Thus, the relatively thin epidermis (~0.1 mm thick) layer was considered negligible in determining the elastic modulus of the relatively much thicker skin layer or dermis (2-3 mm thick). For this reason, a single skin layer was constructed as a skin model to contrast with tumors. Versaflex rubbers CL30 and CL3000 (GLS, McHenry) were chosen as the model tumor and skin materials because their elastic moduli, 230 kPa and 100 kPa, respectively, are relatively close to the elastic moduli of skin tumors and human skin.

The skin layer and the tumor materials were made by first melting the rubber powders in a petri dish followed by de-airing in a vacuum oven and cooling at room temperature. The model tumor material (CL30) was then cut into square tumors of 3 mm×3 mm of various heights and then embedded in the skin layer by first melting the skin layer so that the model tumors could be completely embedded in the model skin. The hypodermis was made by mixing gelatin (Now Foods) at 60° C. at a concentration of 0.12 g/ml. The elastic modulus of the gelatin was about 10 kPa after cooling to room temperature.

The elastic moduli of the bulk model tumor (CL30), model skin (CL3000) and model hypodermal tissue (gelatin) were measured with all three PEFs 10 as 230 kPa, 100 kPa, and 10 kPa. These values were further validated using an Electroforce 3100 (Bose). $E_s$ and $E_t$ denote the elastic modulus of bulk model skin (CL3000), and that of the bulk model tumor (CL30), $E_s$=100±8 kPa and $E_t$=230±20 kPa.

Elastic Modulus Measurements on Phantoms

The elastic modulus of phantom skin which had a 4-mm thick tumor CL30 over a 2 mm or 4 mm thick gelatin layer was determined at more than 20 locations. The elastic modulus of the skin phantom at various locations was about 100±10 kPa as measured by all three PEFs 10, regardless of whether the skin model had a 2 mm or 4 mm hypodermal layer. This indicates that all three PEFs 10 regardless of width could only sense the mechanical response of the harder skin layer. Such an observation was consistent with the fact that in an indentation test (the current PEF test is a flat-punch indentation test) a harder skin layer would take up much of the load causing the lower softer layer to have a negligible effect on the indentation test. To account for this fact, the elastic modulus is presented as normalized by the $E_s$.

Determination of the Elastic Modulus of Phantom Skin Tumors

The phantom tumor samples shown in FIGS. 18(a)-18(d) were subject to elastic modulus measurements using the three PEFs 10 having different contact areas 11. Each PEF 10 measured the elastic moduli of the model tumors at their centers three times. By denoting the elastic modulus of the skin as $E_s$, denoting the elastic modulus measured at the center of each tumor as E, and normalizing E with $E_s$, $E/E_s$ is plotted in FIG. 19 as a function of the tumor thickness as measured by all three PEFs 10. The first data point for zero tumor thickness represented the normalized elastic modulus of the skin. As can be seen, for a PEF 10 with a small contact width of 1 mm, the measured $E/E_s$ increased between tumor thicknesses of 1-2 mm and saturated at about 2.4±0.25 for tumor thicknesses ≥2 mm. For the PEF 10 with a 2 mm contact width, $E/E_s$ increased with an increasing tumor thickness and saturated at about 2.4±0.25 for tumor thicknesses ≥4 mm. For the PEF 10 with a 4 mm contact width, $E/E_s$ increased with an increasing tumor thickness to about 2.4±0.25 when the tumor thickness reached 8 mm. These results indicated that a PEF 10 having a probe 22 with a 1 mm, 2 mm, and 4 mm contact width could differentiate between tumor thicknesses larger than or below 2 mm, 4 mm, and 8 mm, respectively.

Figure 20:
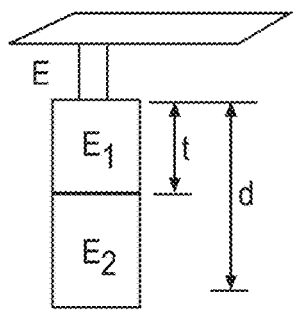
FIG. 20 is a schematic representation of a two spring model.

To estimate the tumor thickness, the tumor and the skin were considered as two springs in series as schematically illustrated in FIG. 20. As can be seen from FIG. 20, the three PEFs 10 with contact area width increments of 1-2 mm created large error bars in the measured tumor thickness. Arrays of PEFs 10 with width increments in the range of 0.1-0.4 mm for the contact areas 11 of the probes 22 would provide better results if used to carry out tumor thickness measurements by substantially reducing the size of the error bars in the measured tumor thickness. Use of a large array of PEFs 10 with the largest possible number of PEFs 10 having contact areas 11 differentiated by the smallest possible width increment or incremental difference in contact area 11 will offer better accuracy in tumor thickness measurements.

The thickness of a melanoma can be obtained by solving the following equation:

$$\frac{t}{E_t} + \frac{d-t}{E_s} = \frac{d}{E}, \quad (5)$$

where E is the elastic modulus measured by a PEF 10, $E_t$ and $E_s$ are the elastic moduli of the tumor and skin, respectively, d is the depth sensitivity of the PEF 10, and t is the tumor thickness. Equation 5 can be normalized by $E_s$ as:

$$\frac{t}{(E_t/E_s)} + \frac{d-t}{1} = \frac{d}{(E/E_s)} \quad (6)$$

Figure 19:
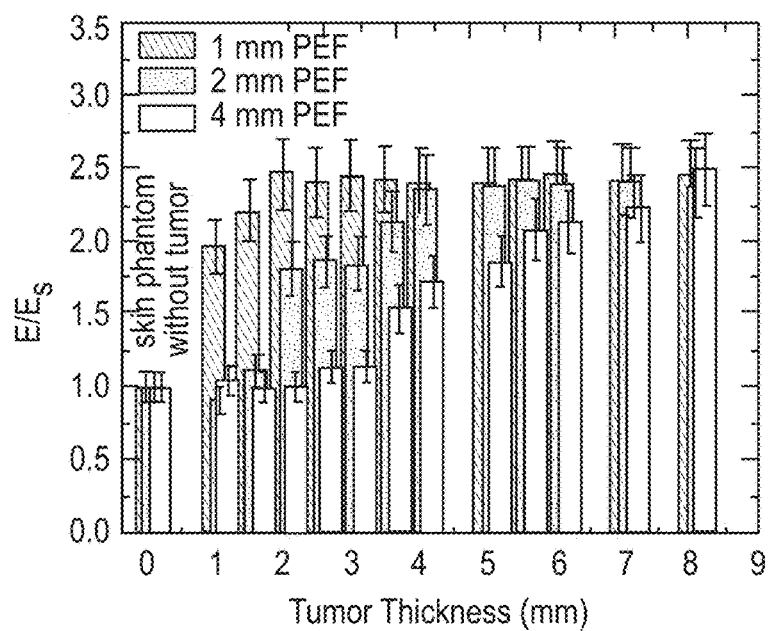
FIG. 19 is a graph showing $E/E_s$ vs. tumor thickness, where E is the measured elastic modulus above the center of a tumor and $E_s$ is the measured elastic modulus of the skin.
Figure 21:
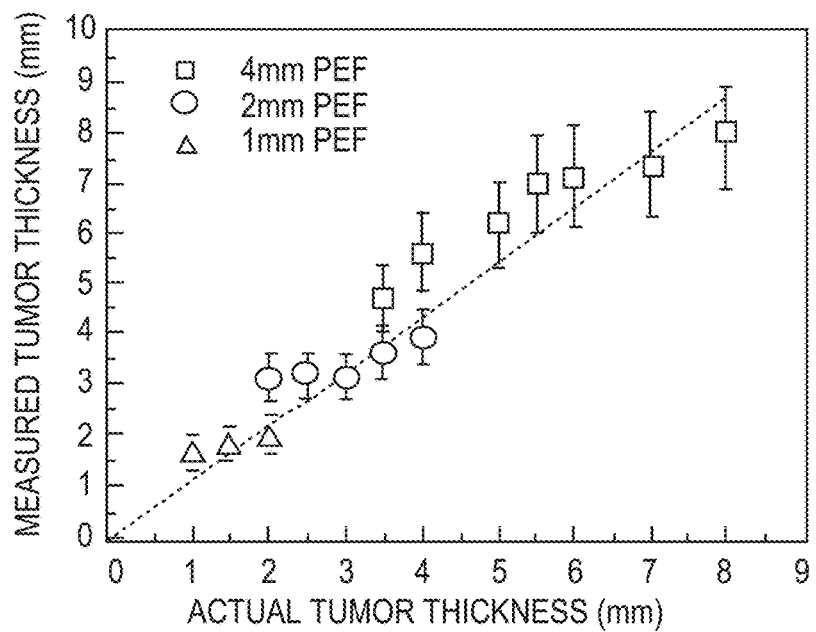
FIG. 21 is a graph of measured tumor thickness (mm) vs. actual tumor thickness (mm).

From FIG. 19, it was noted that the normalized $E_t/E_s$ was 2.4±0.25 for all three PEFs 10 when the tumor thickness exceeded the depth sensitivity. With $E_t/E_s$=2.4±0.25 and d=2, 4 and 8 mm, tumor thicknesses were obtained using Eq. 6 using PEFs with 1 mm, 2 mm, and 4 mm wide contact areas 11 and only the $E/E_s$ of tumors whose thickness is smaller than the depth sensitivity of a PEF 10. The resultant tumor thickness is plotted versus the actual tumor thickness in FIG. 21. As can be seen, using an array of three PEFs 10 having probes 22 with contact areas 11 of different widths of between 1-4 mm, it was possible to determine the tumor thickness for tumors having a thickness in the range of 1-8 mm.

The total height of the gelatin matrix was 34.2±0.8 mm. The clay inclusions in the same row had identical dimensions, but were embedded at different depths. The inclusions in the same column had different heights, but the distances from the gelatin surface to the tops of the inclusions were similar. The exact values of the inclusion dimensions and the depth profiles were measured using a caliper and are listed in Table 2 for comparative purposes.

TABLE 2

Inclusion Dimensions and Inclusion Depths

| | Inclusion dimensions | | | | | | Inclusion depths | | | |
|---|---|---|---|---|---|---|---|---|---|---|
| | Length (mm) | | Width (mm) | | Height (mm) | | $d_1$ (mm) | | $d_2$ (mm) | |
| Inclusion # | Average | SD | Average | SD | Average | SD | Average | SD | Average | SD |
| A1 | 14.53 | 0.26 | 15.20 | 0.40 | 4.87 | 0.35 | 2.22 | 0.28 | 7.09 | 0.45 |
| A2 | 15.24 | 0.38 | 15.26 | 0.20 | 4.98 | 0.29 | 4.09 | 0.33 | 9.07 | 0.44 |
| A3 | 15.36 | 0.25 | 15.14 | 0.37 | 5.24 | 0.31 | 5.94 | 0.26 | 11.18 | 0.40 |
| A4 | 15.90 | 0.35 | 15.17 | 0.23 | 4.97 | 0.42 | 7.21 | 0.32 | 12.18 | 0.53 |
| A5 | 15.23 | 0.25 | 15.21 | 0.30 | 5.23 | 0.29 | 10.34 | 0.30 | 15.57 | 0.42 |
| A6 | 15.36 | 0.26 | 15.55 | 0.24 | 5.30 | 0.28 | 11.92 | 0.21 | 17.22 | 0.35 |
| B1 | 14.51 | 0.39 | 14.63 | 0.40 | 8.47 | 0.34 | 3.03 | 0.28 | 11.50 | 0.44 |
| B2 | 15.19 | 0.20 | 15.18 | 0.35 | 7.97 | 0.32 | 4.07 | 0.39 | 12.04 | 0.50 |
| B3 | 14.72 | 0.21 | 15.76 | 0.29 | 7.23 | 0.29 | 6.45 | 0.32 | 13.68 | 0.43 |
| B4 | 15.40 | 0.31 | 15.69 | 0.37 | 7.45 | 0.35 | 9.55 | 0.38 | 17.00 | 0.52 |
| B5 | 15.62 | 0.24 | 15.46 | 0.38 | 7.69 | 0.31 | 11.79 | 0.33 | 19.48 | 0.45 |
| B6 | 15.62 | 0.39 | 15.27 | 0.20 | 7.71 | 0.31 | 11.95 | 0.41 | 19.66 | 0.51 |
| C1 | 16.19 | 0.38 | 16.04 | 0.35 | 9.43 | 0.27 | 5.27 | 0.26 | 14.70 | 0.37 |
| C2 | 16.15 | 0.27 | 15.32 | 0.24 | 9.66 | 0.30 | 7.00 | 0.33 | 16.66 | 0.45 |
| C3 | 15.88 | 0.28 | 15.42 | 0.30 | 9.45 | 0.33 | 8.34 | 0.31 | 17.79 | 0.45 |
| C4 | 15.67 | 0.21 | 16.07 | 0.30 | 9.29 | 0.33 | 11.21 | 0.48 | 20.50 | 0.58 |
| C5 | 15.95 | 0.28 | 15.71 | 0.32 | 9.83 | 0.27 | 12.18 | 0.28 | 22.01 | 0.39 |
| C6 | 15.85 | 0.39 | 16.18 | 0.26 | 9.73 | 0.34 | 13.67 | 0.40 | 23.40 | 0.52 |
| D1 | 14.71 | 0.35 | 15.40 | 0.22 | 11.40 | 0.35 | 4.22 | 0.30 | 15.62 | 0.46 |
| D2 | 14.66 | 0.29 | 14.89 | 0.33 | 11.58 | 0.29 | 6.66 | 0.28 | 18.24 | 0.40 |
| D3 | 14.64 | 0.22 | 15.18 | 0.34 | 11.68 | 0.34 | 10.45 | 0.37 | 22.13 | 0.50 |
| D4 | 14.85 | 0.28 | 14.95 | 0.36 | 11.57 | 0.31 | 12.13 | 0.28 | 23.70 | 0.42 |
| D5 | 14.81 | 0.20 | 15.08 | 0.34 | 11.72 | 0.32 | 15.06 | 0.30 | 26.78 | 0.44 |
| D6 | 15.20 | 0.40 | 14.83 | 0.37 | 11.68 | 0.36 | 16.24 | 0.31 | 27.92 | 0.48 |
| E1 | 15.79 | 0.25 | 15.74 | 0.33 | 14.82 | 0.30 | 3.19 | 0.32 | 18.01 | 0.44 |
| E2 | 15.77 | 0.38 | 15.75 | 0.31 | 15.04 | 0.27 | 6.44 | 0.29 | 21.48 | 0.40 |
| E3 | 15.81 | 0.34 | 16.05 | 0.28 | 15.12 | 0.30 | 8.58 | 0.44 | 23.70 | 0.53 |
| E4 | 15.40 | 0.35 | 15.71 | 0.38 | 15.11 | 0.32 | 10.30 | 0.29 | 25.41 | 0.43 |
| E5 | 15.74 | 0.39 | 15.71 | 0.31 | 15.17 | 0.36 | 13.58 | 0.43 | 28.75 | 0.56 |
| E6 | 15.66 | 0.30 | 15.64 | 0.35 | 14.78 | 0.35 | 15.59 | 0.39 | 30.37 | 0.52 |

The result of the PEF scan on the model tissue was presented as a color coded elastic modulus map. As an example, maps were generated by PEFs 10, having contact area widths of 6.5±0.2 mm and 9.8±0.3 mm, respectively. The maps illustrate elastic moduli of a gelatin matrix (9-12 kPa), as well as elevated elastic moduli of 14-16 kPa and 18-28 kPa of the clay inclusions. Since the depth sensitivities of the PEFs 10 were different, the elastic modulus values obtained using these PEFs 10 at the same location were distinct. For example, one PEF 10 could only detect the left half part of the inclusions. This was because the PEF 10 had a depth sensitivity of about 13 mm. When the inclusions were more than 13 mm deep from the gelatin surface, they were beyond the detectable depth of that PEF 10. Therefore, that PEF 10 was not able to differentiate the gelatin and inclusions for the right part of the inclusions which were embedded at a depth beyond 13 mm. Since the other PEF 10 had a depth sensitivity of 20 mm, it could detect most of the inclusions. However, the elastic values of the inclusions in the first row measured by the PEF 10 with a 20 mm depth sensitivity were smaller than those measured by the PEF 10 with a depth sensitivity of 13 mm. This was because those inclusions had a small height which was only about 5 mm and thus the entire inclusions were within the depth sensitivity of the PEF 10 with a 20 mm depth sensitivity. Therefore, the PEF 10 with the 20 mm depth sensitivity measured a portion of the sample having a higher proportion of gelatin to inclusion, as compared with the PEF 10 that had only a 13 mm depth sensitivity.

Figure 8:
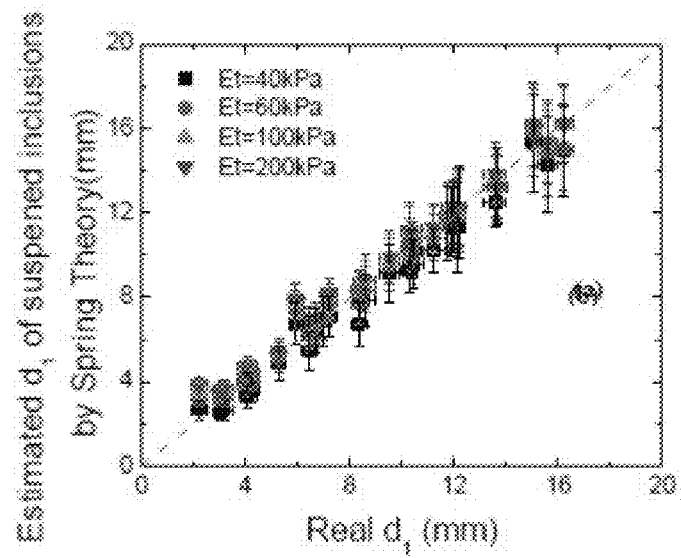
FIG. 8 is a graph depicting estimated depth to the top of an inclusion ($d_1$) using spring theory versus the real values.

The estimated $d_1$ values calculated using the measured E values from PEFs 10 and different $E_t$ values in the spring model were plotted versus the real values in FIG. 8. It is clear that all the data points are close to the dash line which has a slope of 1, which shows that all of the estimated values correlated well with the real values. When $E_t$ was 40 kPa or 60 kPa, which was within the range of the elastic modulus of breast tumors, the estimations of the $d_1$ values were quite good. When $E_t$ was 100 kPa or 200 kPa, which is much larger than the elastic modulus of breast tumors, the estimations were not very different from the real values. This shows that the estimation of $d_1$ is not sensitive to the assumed $E_t$ values. This demonstrates that it is feasible to use a range of $E_t$ values to deduce $d_1$ values.

Figure 9:
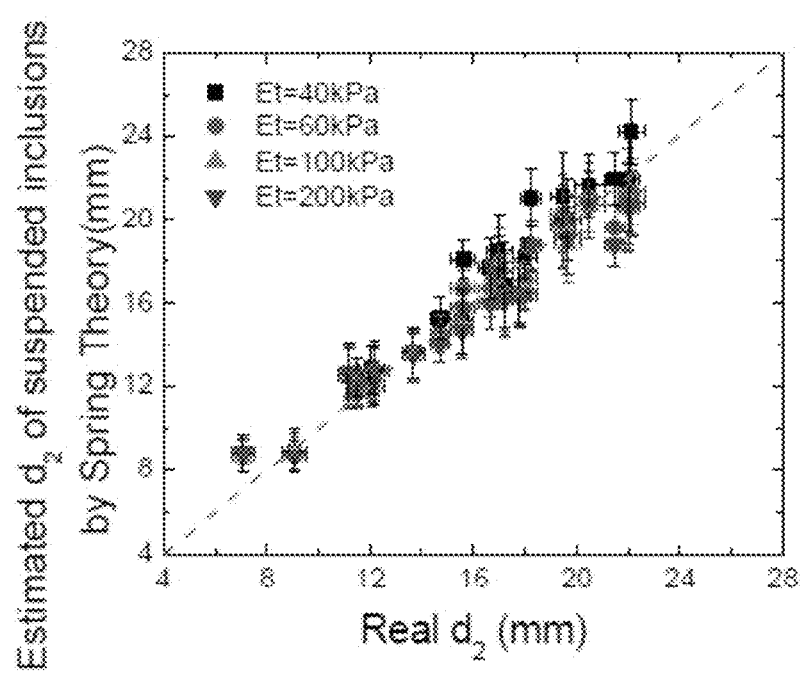
FIG. 9 is a graph showing estimated depth to the bottom of an inclusion ($d_2$) using spring theory versus real values.
Figure 10A:
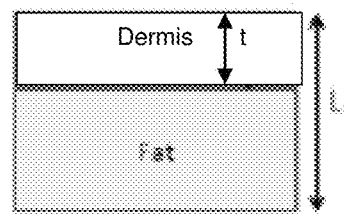
FIG. 10A is a schematic diagram of skin and fat.
Figure 10B:
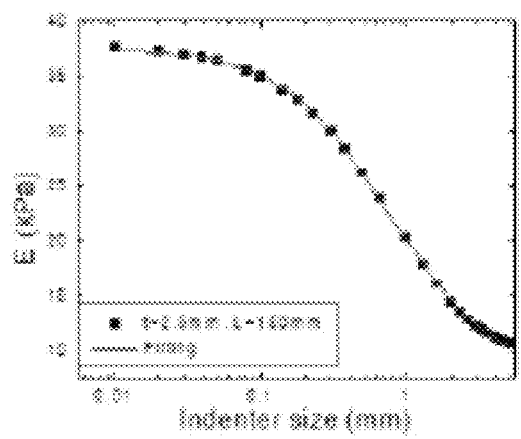
FIG. 10B is a graph showing the E (kPa) v. indenter size.
Figure 11A:
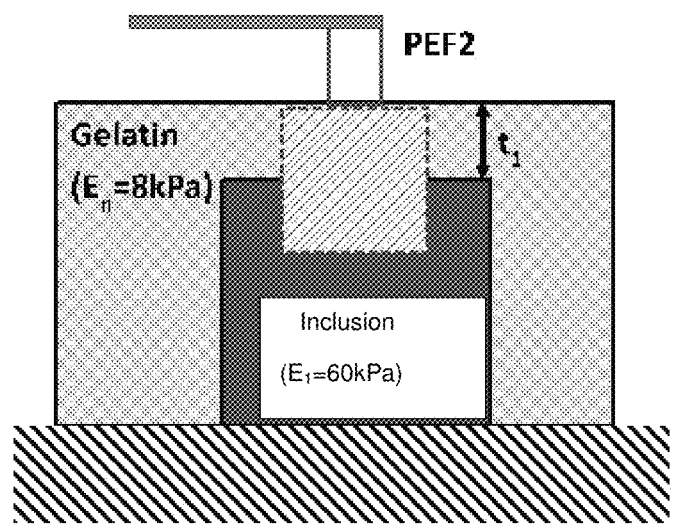
FIG. 11A is diagram showing the probe and skin/fat thickness.
Figure 11B:
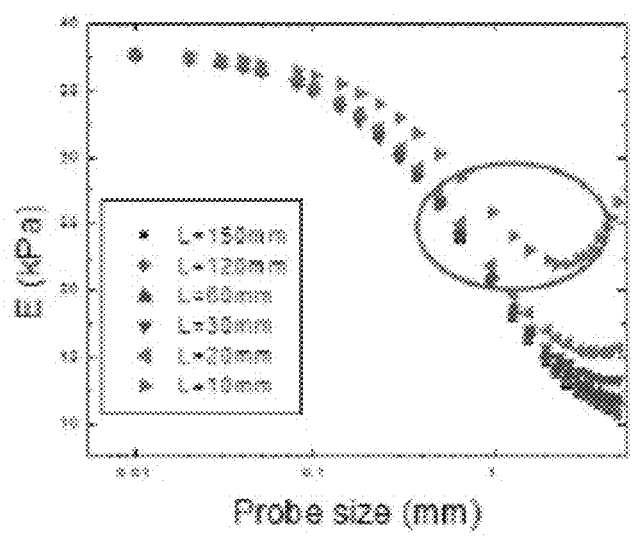
FIG. 11B is a diagram of the E (kPa) v. probe contact area size.
Figure 12A:
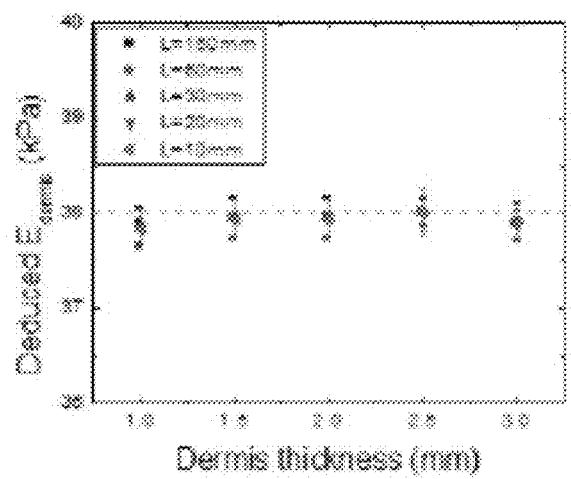
FIG. 12A is graph showing deduced $E_{dermis}$ vs. dermis thickness.
Figure 12B:
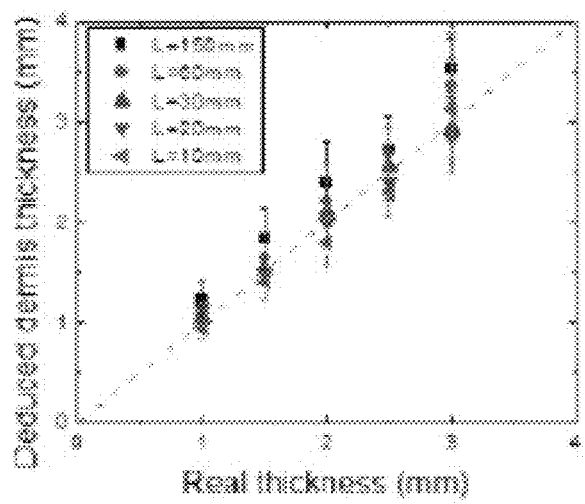
FIG. 12B is a graph showing deduced dermis thickness v. real thickness.
Figure 13A:
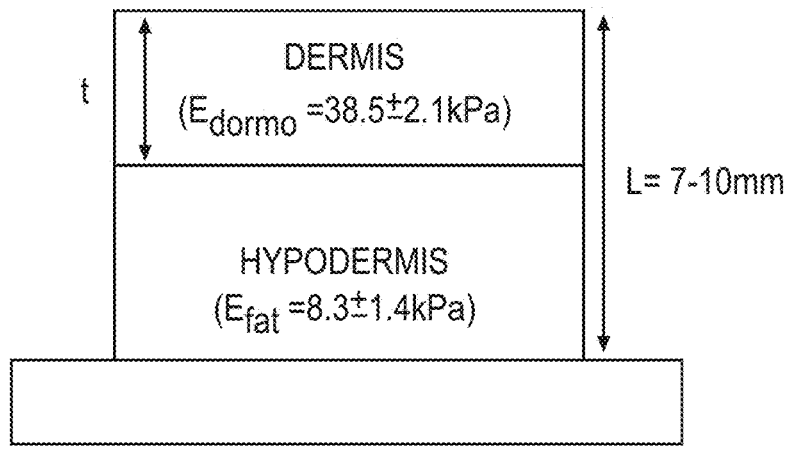
FIG. 13A is a diagram of the dermis and hypodermis.
Figure 13B:
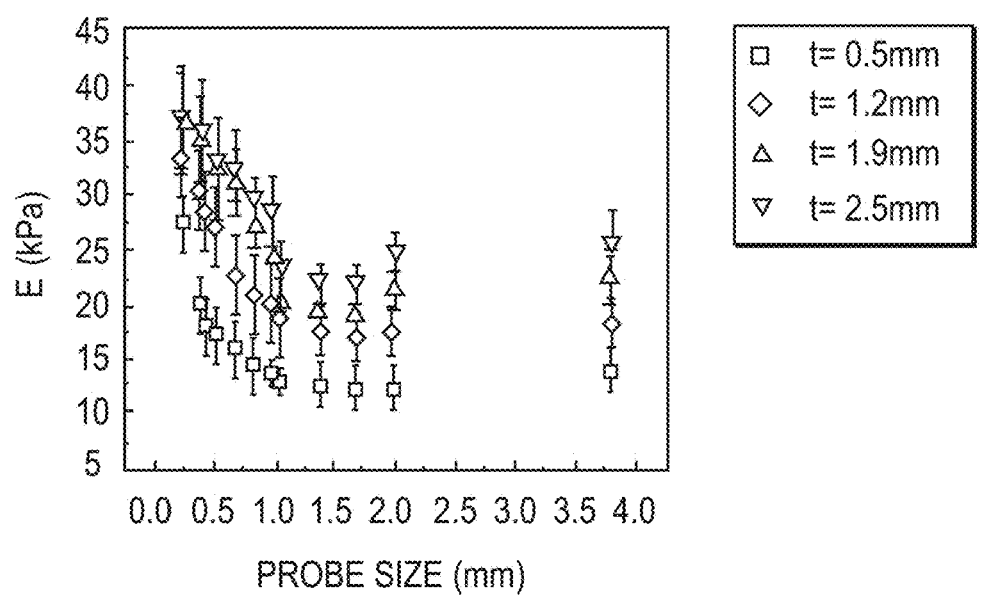
FIG. 13B is a graph showing E (kPa) v. probe contact area size.
Figure 14A:
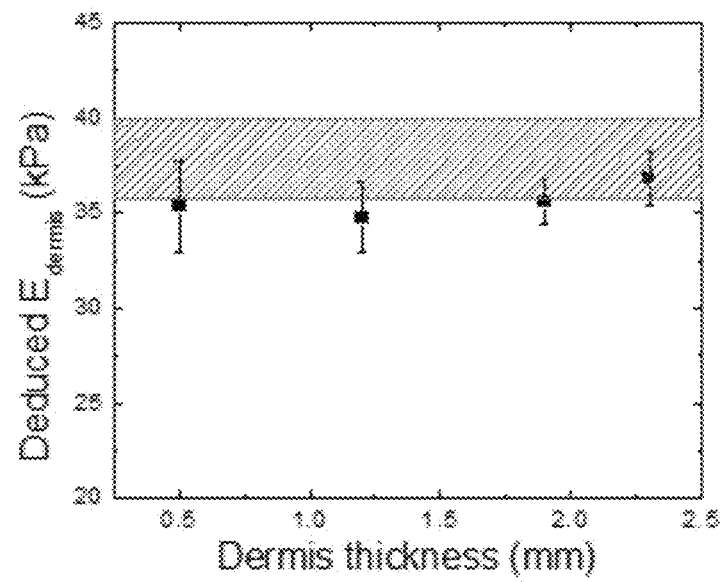
FIG. 14A is a graph showing deduced $E_{dermis}$ (kPa) v. dermis thickness.
Figure 14B:
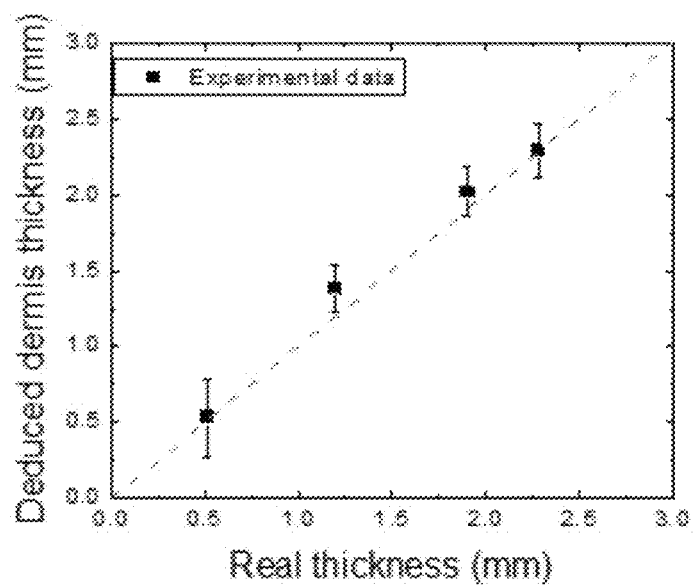
FIG. 14B is a graph showing deduced $E_{dermis}$ (kPa) v. real thickness.

The estimated $d_2$ values deduced by use of the spring model plotted versus the real values are shown in FIG. 9. The results were consistent with the results discussed above for $d_1$ in that the estimation of the depth profile was not sensitive to the assumed $E_t$ values.

Figure 22:
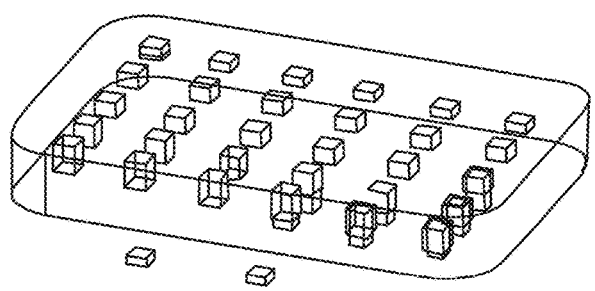
FIG. 22 is a schematic representation of a gelatin model with suspended inclusions.

A schematic representation of the gelatin model is shown in FIG. 22. The darker shaded cuboids show the exact locations of the inclusions, while the lighter shaded cuboids represent the predicted sizes and locations of the inclusions. It should be noted that the predicted sizes and locations were averaged values, since multiple Et were used values for the calculations. The lighter shaded cuboids overlapped with the darker shaded cuboids for most of the inclusions. Therefore, the deduced 3D profiles of the inclusions were quite accurate.

For some inclusions, because their $d_2$ values were larger than the maximum depth sensitivity of PEFs 10, $d_2$ could not be assessed using the four PEFs 10 that were employed in this study. By using the four PEFs 10 listed in Table 1, the depth profiles of the inclusions could be deduced for inclusions that were less than 2 cm deep, which was sufficient for tumors in a normal size breast but not for tumors whose bottom surfaces could be more than 2 cm deep. For larger breasts and deeper tumors, PEFs with a larger contact width can be used to allow for measurements at greater depths.

Example of Measuring Stiffness and Thickness of the Dermis in Skin

In the example discussed below, all of the PEFs 10 were hand-built. The top piezoelectric layer 12 and bottom piezoelectric layer 14 were both PZT layers, which were made of PZT 5H4E material (Piezo Systems Inc., Cambridge, Mass.). In this example both the top piezoelectric layer 12 and the bottom piezoelectric layer 14 were 127 µm thick. Stainless steel (Alfa Aesar, War Hill, Mass.), which was 50 µm thick, was used as the non-piezoelectric layer 16. The top piezoelectric layer 12 was 22 mm long and 3.5 mm wide. The bottom piezoelectric layer 14 was 12 mm long and 3.5 mm wide. The non-piezoelectric layer 16 of stainless steel was 32 mm long and 3.5 mm wide. The top piezoelectric layer 12, bottom piezoelectric layer 14 and non-piezoelectric layer 16 were bonded together using insulating epoxy along the edges, and a very small patch of conductive epoxy was used at the center of the top piezoelectric layer 12 and bottom piezoelectric layer 14. After curing overnight, probes 22 having cylindrical contact areas of different sizes, were bonded to the partially assembled PEF 10 using insulating glue. The probes 22 were made from wires of different diameters. The wires were cut into 10 mm-long segments using a wire saw, so that the surfaces of contact areas 11 of the probes 22 were very smooth. The radiuses of the probes 22 are shown in Table 3.

TABLE 3

The Radiuses of the PEF probes

| PEF# | Probe Radius (mm) |
|---|---|
| 1 | 0.23 ± 0.01 |
| 2 | 0.38 ± 0.01 |
| 3 | 0.42 ± 0.01 |
| 4 | 0.52 ± 0.01 |
| 5 | 0.66 ± 0.01 |
| 6 | 0.83 ± 0.01 |
| 7 | 0.98 ± 0.01 |
| 8 | 1.05 ± 0.11 |
| 9 | 1.38 ± 0.05 |
| 10 | 1.68 ± 0.02 |
| 11 | 2.00 ± 0.01 |
| 12 | 3.80 ± 0.11 |

Versaflex (GLS, McHenry, Ill.) samples of soft polymer with varying mechanical properties were employed. The Versaflex CL2003 soft polymer samples were made to mimic the dermis layer of the skin. The elastic modulus of the Versaflex CL2003 was 38 kPa, as determined by previous experiments. The samples as obtained from the manufacturer were in the form of small grains having a grain size of about 5 mm. A selected weight of Versaflex CL2003 grains was melted in a petri dish and cooled down to solidify. The melting temperature was 180° C. To eliminate the bubbles in the sample, all the procedures were done in a vacuum oven. When the temperature inside the oven became higher than the melting temperature, the grains began to melt. At that time, the vacuum pump was started and the bubbles inside the samples could be eliminated. With this method, Versaflex CL2003 samples with different thicknesses were fabricated. The diameter of each of the samples was 88 mm.

Skin phantoms were then made using Versaflex CL2003 and gelatin. The skin phantoms consisted of a thin Versaflex CL2003 film and a gelatin substrate. First, a thin layer of Versaflex CL2003 was made in a petri dish. After the polymer was solidified, a gelatin solution (0.08 g/mL, E=8 kPa) was poured into the same petri dish. After the gelatin was solidified, the entire phantom was taken out of the dish and flipped over. With this method, the film and the substrate were bonded while removing all bubbles in between them.

Axisymmetric simulations were used in ABAQUS, since both the sample and the probe 22 of the PEF 10 were cylinders. The elastic modulus of the dermis layer was defined as 38 kPa and 100 kPa for different simulations. The elastic modulus of the fat layer was set as 8 kPa in all simulations. The thicknesses of the dermis layers in the simulations were set as 1.0 mm, 1.5 mm, 2.0 mm, 2.5 mm, and 3.0 mm. For each dermis thickness, the total thickness of the skin phantom was defined as 10 mm, 20 mm, 30 mm, 60 mm, and 150 mm. The bottom of the sample was fixed in three dimensions. A constant displacement, 10 µm, was applied to the contact area of the sample and the probe 22 of the PEF 10 to simulate the indentation of the PEF 10. The resulting reaction forces on the sample surface were exported and used to calculate the measured elastic modulus using the following equation:

$$E = \frac{(1 - v^2)F}{2ad} \qquad (7)$$

where E is the effective elastic modulus; v is the Poisson's ratio, which was defined as 0.5 in the simulation; F is the reaction force on the sample surface; a is the radius of the contact area 11 of probe 22; and d is the indentation depth, which was defined as 10 µm.

Figure 23:
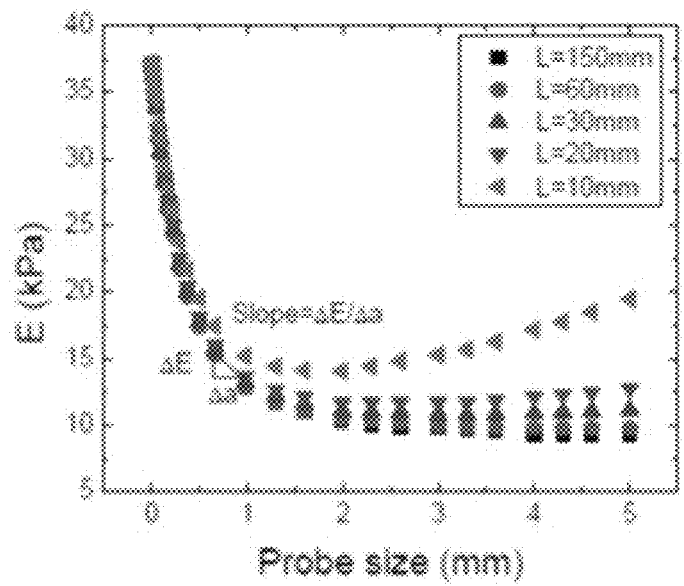
FIG. 23 is a graph of E (kPa) vs. probe contact area size.

The effective elastic moduli calculated from the simulation results were plotted against the sizes of the contact areas 11 of the probes 22. As an example, the plot of E vs. the sizes of the contact areas 11 of the probes 22 when the dermis thickness is 1.0 mm is shown in FIG. 23. The elastic modulus decreases as a function of the increasing size of the contact area 11 of the probe 22. This is because when a PEF 10 with a larger contact area 11 is used, it is able to measure a deeper area in the sample which consists of a stiff top layer (38 kPa) and a soft substrate (8 kPa). The larger the contact area 11, the more substrate it detects, and thus the smaller the measured elastic modulus will be. When the contact area 11 is large enough, most of the detectable area is the soft substrate, and therefore the elastic modulus saturates. However, when the total thickness is small (for example L=10 mm) and the size of the contact area 11 of the probe 22 is large enough, the elastic modulus increases with the size of the contact area 11 of the probe 22. This is because in the simulation, the bottom of the phantom was defined as fixed which is similar to a situation where the phantom is placed on a very rigid surface. When the size of the contact area 11 of the probe 22 is very large, the PEF 10 can detect the very rigid surface below the phantom and thus the measured elastic modulus increases.

An empirical formula derived from Green's function was used to deduce the elastic modulus and thickness of the dermis. This analysis is based on the indentation being in a semi-infinite phantom. The elastic modulus from indentation (E) can be calculated using the formula:

$$E = E_d + \frac{E_f - E_d}{1 + (tx_0/a)^n} \qquad (8)$$

in which $E_d$ is the elastic modulus of the dermis layer; $E_f$ is the elastic modulus of the fat layer; a is the radius of the indenter; t is the thickness of the film; and both n and $x_0$ are parameters which vary with the modulus mismatch $\beta=E_f/E_d$. The parameter $x_0$ can be calculated using the following formula:

$$\log(x_0) = -0.093 + 0.792 \log(E_s/E_f) + 0.05(\log(E_s/E_f))^2 \quad (9)$$

The value of n does not change much when the mismatch ratio is between about 0.01 to about 100.

This formula is based on the assumption of using semi-infinite samples. However, the samples in the simulation and experiments are all finite. The effective elastic modulus measured from the indentation could thus be affected by a rigid surface located underneath the phantoms. Therefore, the data affected by the rigid surface needs to be excluded in the formula fitting.

Figure 24:
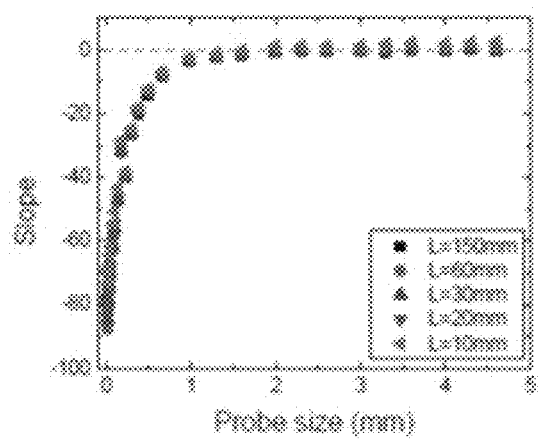
FIG. 24 is a graph of the slope of E vs. probe contact area size.

The criteria used is the slope of E versus probe size, which is calculated by dividing the E difference ($\Delta E$) by the difference in the probe contact area sizes ($\Delta a$) between two adjacent data points as shown in FIG. 23. The calculated slope was plotted versus the size of contact area 11 of the probe 22 in FIG. 24.

When the slope is smaller than 0, the elastic modulus decreases with the size of the contact area 11 of the probe 22. In this instance, the PEF 10 has not detected the rigid surface underneath the phantom sample and thus this data should be included in the curve fit. When the slope is larger than 0, the elastic modulus increases with the size of the contact area 11 of the probe 22, which indicates that the data was affected by the rigid surface underneath the phantom sample and thus should be excluded in the curve fit.

Figure 25:
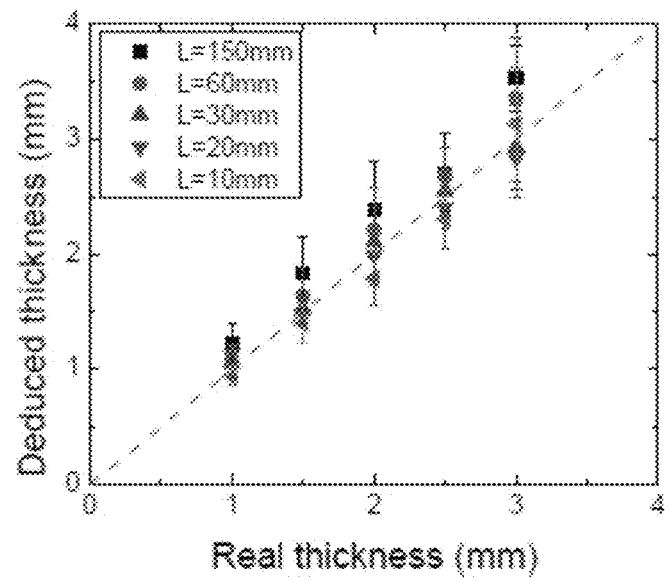
FIG. 25 is a graph showing deduced thickness (mm) vs. real thickness (mm).

As an example, the deduced $E_f$, $E_d$, and t using different slopes as criteria is shown in Table 4. The elastic moduli of the dermis and fat were 38 kPa and 8 kPa, respectively. The dermis thickness was 1.0 mm. As can be seen, no matter which slope is used, the deduced elastic modulus of dermis is always close to the real value. However, when the slope increases, the deduced dermis thickness gets closer to the real value. The closer the slope gets to 0, the more accurate the deduced value of the dermis thickness becomes. When the slope is larger than 0, the difference between the deduced dermis thickness and the real value increases. By analyzing the data from different skin phantoms, averaging the deduced t values when the slope is between −1.5 and 0 gave best results. The deduced dermis thickness is plotted versus the real values from simulation is plotted in FIG. 25. As can be seen, no matter how thin the phantom is, the data points are all close to the dashed line which has a slope of 1. Therefore, this criteria and method can be used to deduce both the elastic modulus and thickness of the dermis.

TABLE 4

The deduced $E_f$, $E_d$, and t using slope as the criteria to include data for curve fitting

| Max Probe size (mm) | slope | $E_{fat}$ (kPa) AVE | SD | $E_{dermis}$ (kPa) AVE | SD | t (mm) AVE | SD | t_error |
|---|---|---|---|---|---|---|---|---|
| 0.66 | −7.56 | 4.62 | 1.32 | 37.86 | 0.20 | 2.00 | 0.18 | 99.56% |
| 1.0 | −3.33 | 6.17 | 0.72 | 37.72 | 0.18 | 1.49 | 0.10 | 48.83% |
| 1.3 | −1.99 | 7.29 | 0.52 | 37.58 | 0.19 | 1.24 | 0.07 | 23.77% |
| 1.6 | −1.30 | 7.89 | 0.41 | 37.49 | 0.19 | 1.13 | 0.06 | 12.68% |
| 2.0 | −0.25 | 8.48 | 0.34 | 37.17 | 0.24 | 1.04 | 0.06 | 4.35% |
| 2.3 | −0.25 | 8.66 | 0.30 | 37.32 | 0.21 | 1.01 | 0.05 | 0.64% |
| 2.6 | −0.26 | 8.94 | 0.27 | 37.25 | 0.22 | 0.97 | 0.05 | −3.23% |
| 3.0 | −0.19 | 9.16 | 0.25 | 37.18 | 0.22 | 0.94 | 0.05 | −6.15% |
| 3.3 | 0.12 | 9.33 | 0.23 | 37.13 | 0.23 | 0.92 | 0.05 | −8.20% |
| 3.6 | 0.30 | 9.47 | 0.21 | 37.08 | 0.23 | 0.90 | 0.05 | −10.00% |
| 4.0 | 0.12 | 9.63 | 0.20 | 37.02 | 0.24 | 0.88 | 0.05 | −11.88% |
| 4.3 | 0.24 | 9.77 | 0.20 | 36.97 | 0.25 | 0.87 | 0.05 | −13.41% |
| 4.6 | 0.31 | 9.89 | 0.19 | 36.92 | 0.26 | 0.85 | 0.05 | −14.76% |
| 5.0 |  | 10.02 | 0.19 | 36.87 | 0.28 | 0.84 | 0.05 | −16.09% |

This methodology has also been applied to experimental data to deduce the elastic modulus and thickness of the dermis in a skin phantom. The same criteria and method was applied to the experimental data. The elastic moduli of the dermis and fat in the skin phantom were 38 kPa and 8 kPa, respectively. The deduced elastic moduli of the dermis and fat and the deduced thickness of the dermis are shown in Table 5.

TABLE 5

The deduced elastic moduli of dermis and fat and thickness of the dermis

| | $E_{fat}$ (kPa) AVE | SD | $E_{dermis}$ (kPa) AVE | SD | t (mm) AVE | SD |
|---|---|---|---|---|---|---|
| t = 0.5 mm | 9.41 | 2.58 | 35.32 | 2.39 | 0.53 | 0.26 |
| t = 1.2 mm | 11.65 | 1.46 | 34.75 | 1.87 | 1.38 | 0.15 |
| t = 1.9 mm | 12.37 | 1.75 | 34.56 | 1.18 | 2.02 | 0.16 |
| t = 2.3 mm | 15.46 | 1.49 | 34.80 | 1.37 | 2.29 | 0.18 |

Figure 26:
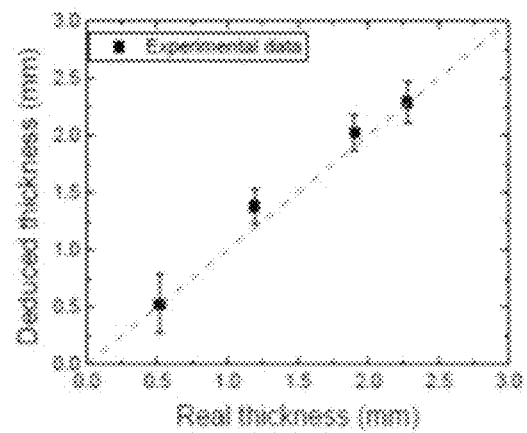
FIG. 26 is a graph of deduced thickness (mm) vs. the real thickness for the skin phantoms.

Although the deduced elastic moduli of yjr fat can be much larger than the real values, the deduced elastic moduli of the dermis are quite accurate. The deduced dermis thickness is plotted versus the real thickness (as measured by caliper) in FIG. 26. FIG. 26 shows that the four data points are very close to the dash line which has a slope of 1. Therefore, the deduced dermis thickness closes agrees with the real value.

It is thus feasible to determine the thickness and elastic modulus of the dermis in skin phantoms. When the size of the contact area 11 of the probe 22 is large, the measured elastic modulus from indentation is affected by the rigid surface beneath the phantom. Therefore, the slope of E versus the size of the probe 22 may be used as a criterion to exclude the affected data for analysis. When the slope is between −1.5 and 0, the measured elastic moduli are plotted versus probe size and fitted to an empirical formula derived from Green's function to deduce the thickness and elastic modulus of the dermis. The deduced elastic modulus of dermis is very close to the real value. The averaged dermis thickness when the slope is between −1.5 and 0 agrees with the real value for both simulations and experiments.

It is to be understood, however, that even though numerous characteristics and advantages of the present invention have been set forth in the foregoing description, together with details of the method, composition and function of the invention, the disclosure is illustrative only, and changes may be made in detail, within the principles of the invention to the full extent indicated by the broad general meaning of the terms in which the appended claims are expressed.

Unless stated otherwise, terms such as "first" and "second" are used to arbitrarily distinguish between the elements such terms describe. Thus, these terms are not necessarily intended to indicate temporal or other prioritization of such elements. Further, the use of introductory phrases such as "at least one" and "one or more" in the claims should not be construed to imply that the introduction of another claim element by the indefinite articles "a" or "an" limits any particular claim containing such introduced claim element to inventions containing only one such element, even when the same claim includes the introductory phrases "one or more" or "at least one" and indefinite articles such as "a" or "an." The same holds true for the use of definite articles.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

In this specification including any claims, the term "each" may be used to refer to one or more specified characteristics of a plurality of previously recited elements or steps. When used with the open-ended term "comprising," the recitation of the term "each" does not exclude additional, unrecited elements or steps. Thus, it will be understood that an apparatus may have additional, unrecited elements and a method may have additional, unrecited steps, where the additional, unrecited elements or steps do not have the one or more specified characteristics.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

Other embodiments of the present disclosure will be apparent to those skilled in the art from consideration of the specification and practice of the embodiments disclosed herein. It is intended that the specification and examples be considered as exemplary only, with a true scope of the disclosure being indicated by the following claims.

All documents mentioned herein are hereby incorporated by reference in their entirety or alternatively to provide the disclosure for which they were specifically relied upon.

The foregoing embodiments are susceptible to considerable variation in practice. Accordingly, the embodiments are not intended to be limited to the specific exemplifications set forth hereinabove. Rather, the foregoing embodiments are within the spirit and scope of the appended claims, including the equivalents thereof available as a matter of law.

The applicant(s) do not intend to dedicate any disclosed embodiments to the public, and to the extent any disclosed modifications or alterations may not literally fall within the scope of the claims, they are considered to be part hereof under the doctrine of equivalents.

The following references are cited and included herein by reference.

[1] A. C. Society. (2012). *What are the key statistics about melanoma skin cancer.* Available: http://www.cancer.org/cancer/skincancer-melanoma/detailedguide/melanoma-skin-cancer-key-statistics

[2] A. J. Miller and M. C. Mihm Jr, "Melanoma," *New England Journal of Medicine*, vol. 355, pp. 51-65, 2006.

[3] K. M. Rubin, "Melanoma Staging: A Review of the Revised American Joint Committee on Cancer Guidelines," *Journal of the Dermatology Nurses' Association*, vol. 2, pp. 254-259, 2010.

[4] C. M. Balch, J. E. Gershenwald, S.-j. Soong, J. F. Thompson, M. B. Atkins, D. R. Byrd, et al., "Final version of 2009 AJCC melanoma staging and classification," *Journal of Clinical Oncology*, vol. 27, pp. 6199-6206, 2009.

[5] A. A. Marghoob, L. Changchien, J. DeFazio, W. C. Dessio, J. Malvehy, I. Zalaudek, et al., "The most common challenges in melanoma diagnosis and how to avoid them," *Australasian Journal of Dermatology*, vol. 50, pp. 1-13, 2009.

[6] J. F. Thompson, R. A. Scolyer, and R. F. Kefford, "Cutaneous melanoma," *The Lancet*, vol. 365, pp. 687-701, 2005.

[7] A. C. Halpern and J. A. Lieb, "Early melanoma diagnosis: a success story that leaves room for improvement," *Current opinion in oncology*, vol. 19, pp. 109-115, 2007.

[8] C. A. Charles, V. S. Yee, S. W. Dusza, A. A. Marghoob, S. A. Oliveria, A. Kopf, et al., "Variation in the diagnosis, treatment, and management of melanoma in situ: a survey of US dermatologists," *Archives of dermatology*, vol. 141, pp. 723-729, 2005.

[9] A. C. Society. (2013). *Key Statistics about Breast Cancer* Available: http://www.cancer.org/cancer/breastcancer/detailedguide/breast-cancer-key-statistics

[10] W. H. Organization. (2011). *Breast cancer: prevention and control*. Available: http://www.who.int/cancer/detection/breastcancer/en/index.html

[11] L. Dummin, M. Cox, and L. Plant, "Prediction of breast tumor size by mammography and sonography—a breast screen experience," *The Breast*, vol. 16, pp. 38-46, 2007.

[12] M. B. Barton, R. Harris, and S. W. Fletcher, "Does this patient have breast cancer?," *JAMA: the journal of the American Medical Association*, vol. 282, p. 1270, 1999.

[13] W. H. Goodson III, N. A. Grissom, D. H. Moore II, and F. M. Dirbas, "Streamlining clinical breast examination," *Journal of the National Cancer Institute*, vol. 97, pp. 1476-1477, 2005.

[14] P. Weatherall, G. F. Evans, G. J. Metzger, M. H. Saborrian, and A. M. Leitch, "MRI vs. histologic measurement of breast cancer following chemotherapy: Comparison with x-ray mammography and palpation," *Journal of Magnetic Resonance Imaging*, vol. 13, pp. 868-875, 2001.

[15] I. Mittra, M. Baum, H. Thornton, and J. Houghton, "Is clinical breast examination an acceptable alternative to mammographic screening?," *Bmj*, vol. 321, pp. 1071-1073, 2000.

[16] D. Förnvik, S. Zackrisson, O. Ljungberg, T. Svahn, P. Timberg, A. Tingberg, et al., "Breast tomosynthesis: Accuracy of tumor measurement compared with digital mammography and ultrasonography," *Acta Radiologica*, vol. 51, pp. 240-247, 2010.

[17] B. Pritt, T. Ashikaga, R. G. Oppenheimer, and D. L. Weaver, "Influence of breast cancer histology on the

[18] A. M. Bosch, A. G. Kessels, G. L. Beets, J. D. Rupa, D. Koster, J. van Engelshoven, et al., "Preoperative estimation of the pathological breast tumour size by physical examination, mammography and ultrasound: a prospective study on 105 invasive tumours," *European journal of radiology*, vol. 48, pp. 285-292, 2003.

[19] S. Allen, W. Cunliffe, J. Gray, J. Liston, L. Lunt, L. Webb, et al., "Pre-operative estimation of primary breast cancer size: a comparison of clinical assessment, mammography and ultrasound," *The Breast*, vol. 10, pp. 299-305, 2001.

[20] L. H. Vanderwalde, C. M. Dang, C. Bresee, and E. H. Phillips, "Discordance between pathologic and radiologic tumor size on breast MRI may contribute to increased re-excision rates," *The American surgeon*, vol. 77, pp. 1361-1363, 2011.

[21] A. Sarvazyan, "Mechanical imaging: a new technology for medical diagnostics," *International journal of medical informatics*, vol. 49, p. 195, 1998.

[22] V. Egorov and A. P. Sarvazyan, "Mechanical imaging of the breast," *Medical Imaging, IEEE Transactions on*, vol. 27, pp. 1275-1287, 2008.

[23] V. Egorov, T. Kearney, S. B. Pollak, C. Rohatgi, N. Sarvazyan, S. Airapetian, et al., "Differentiation of benign and malignant breast lesions by mechanical imaging," *Breast cancer research and treatment*, vol. 118, pp. 67-80, 2009.

[24] J. H. Lee and C. H. Won, "Inclusion mechanical property estimation using tactile images, finite element method, and artificial neural network," in *Annual International Conference of the IEEE*, 2011, pp. 14-17.

[25] J. Lee and C. Won, "High resolution tactile imaging sensor using total internal reflection and non-rigid pattern matching algorithm," *Sensors Journal, IEEE*, pp. 1-1, 2011.

[26] J. Lee and C. Won, "Tactile Sensation Imaging System for Embedded Lesion Characterization," 2013.

[27] L. Liberman, A. F. Abramson, F. B. Squires, J. Glassman, E. Morris, and D. Dershaw, "The breast imaging reporting and data system: positive predictive value of mammographic features and final assessment categories," *AJR. American journal of roentgenology*, vol. 171, pp. 35-40, 1998.

[28] S. K. Davis, B. D. Van Veen, S. C. Hagness, and F. Kelcz, "Breast tumor characterization based on ultrawideband microwave backscatter," *Biomedical Engineering, IEEE Transactions on*, vol. 55, pp. 237-246, 2008.

[29] A. Markidou, W. Y. Shih, and W. H. Shih, "Soft-materials elastic and shear moduli measurement using piezoelectric cantilevers," *Review of scientific instruments*, vol. 76, p. 064302, 2005.

[30] H. O. Yegingil, W. Y. Shih, W. Anjum, A. D. Brooks, and W. H. Shih, "Soft tissue elastic modulus measurement and tumor detection using piezoelectric fingers," in *MRS Fall Meeting*, 2005.

[31] H. Yegingil, W. Y. Shih, and W. H. Shih, "Probing elastic modulus and depth of bottom-supported inclusions in model tissues using piezoelectric cantilevers," *Review of scientific instruments*, vol. 78, p. 115101, 2007.

[32] S. T. Szewczyk, W. Y. Shih, and W. H. Shih, "Palpationlike soft-material elastic modulus measurement using piezoelectric cantilevers," *Review of scientific instruments*, vol. 77, p. 044302, 2006.

[33] X. Xu, C. Gifford-Hollingsworth, R. Sensenig, W.-H. Shih, W. Y. Shih, and A. D. Brooks, "Breast Tumor Detection Using Piezoelectric Fingers: First Clinical Report," *Journal of the American College of Surgeons*, 2013.

[34] H. O. Yegingil, "Breast cancer detection and differentiation using piezoelectric fingers," Drexel University, 2009.

[35] T. A. Krouskop, T. M. Wheeler, F. Kallel, B. S. Garra, and T. Hall, "Elastic moduli of breast and prostate tissues under compression," *Ultrasonic imaging*, vol. 20, pp. 260-274, 1998.

[36] A. Samani and D. Plewes, "An inverse problem solution for measuring the elastic modulus of intact ex vivo breast tissue tumours," *Physics in medicine and biology*, vol. 52, p. 1247, 2007.

[37] A. Samani, J. Zubovits, and D. Plewes, "Elastic moduli of normal and pathological human breast tissues: an inversion-technique-based investigation of 169 samples," *Physics in medicine and biology*, vol. 52, p. 1565, 2007.

[38] H. Mehrabian, G. Campbell, and A. Samani, "A constrained reconstruction technique of hyperelasticity parameters for breast cancer assessment," *Physics in medicine and biology*, vol. 55, p. 7489, 2010.

[39] J. J. O'Hagan and A. Samani, "Measurement of the hyperelastic properties of 44 pathological ex vivo breast tissue samples," *Physics in medicine and biology*, vol. 54, p. 2557, 2009.

[40] J. J. O'Hagan and A. Samani, "Measurement of the hyperelastic properties of tissue slices with tumour inclusion," *Physics in medicine and biology*, vol. 53, p. 7087, 2008.

What is claimed is:

1. A device for three dimensional tumor location in tissue, said device comprising:
    an array including at least three piezoelectric fingers wherein each piezoelectric finger comprises:
        a first piezoelectric layer having a first length and being configured for application of a voltage thereto;
        a second sensing piezoelectric layer having a second length shorter than said first length;
        a non-piezoelectric layer, a proximal portion of which is located between the first and second piezoelectric layers; and
        a probe having a contact area and being located at a distal end of the non-piezoelectric layer or a distal end of one said piezoelectric layer;
        wherein each said probe has a contact area with a different size than a size of a contact area of every other of said probes, and the area of each said contact area is greater than $0.01$ mm$^2$;
    a measuring means for:
        (a) measuring a voltage induced across said sensing piezoelectric layer with each of said probes at a particular location on a surface of the tissue to obtain a plurality of measured induced voltages for that location,
        (b) determining an elastic modulus of the tissue from each said measured induced voltage, and
        (c) displaying the determined elastic moduli of the tissue in three dimensions.

2. The device of claim 1, where each contact area has a width and a difference in the width of each contact area is between 0.1-0.4 mm.

3. The device of claim 1, comprising at least four said piezoelectric fingers, and wherein the at least four differently sized contact areas are sized to provide a measurement for determining $d_1$ and $d_2$, wherein $d_1$ is the distance from the surface to a top of an object and $d_2$ is the distance from the surface to a bottom of the object.

4. The device of claim 1, wherein the contact area of each said probe is in a range of from 10-100 mm².

5. The device of claim 1, wherein the contact area of each said probe is in a range of 0.01-50 mm².

6. The device as claimed in claim 1, wherein when the distance from a surface of the tissue to a bottom of an inclusion in the tissue is larger than a depth sensitivity of one said probe, the elastic modulus for the measured induced voltage from that probe is determined using a two-spring model.

7. The device as claimed in claim 6, wherein the elastic modulus E determined by the two-spring model is expressed as:

$$\frac{h}{E} = \frac{d_1}{E_n} + \frac{h - d_1}{E_t}$$

where h is the depth sensitivity of the probe; $d_1$ is the distance from the surface of the tissue to a top of the inclusion; and $E_n$ and $E_t$ are the elastic moduli of normal tissue and of the inclusion, respectively.

8. The device as claimed in claim 1, wherein when the distance from a surface of the tissue to a bottom of an inclusion in the tissue is smaller than a depth sensitivity of one said probe, the elastic modulus for the measured induced voltage from that probe is determined using a three-spring model.

9. The device as claimed in claim 8, wherein the elastic modulus E determined by the two-spring model is expressed as:

$$\frac{h}{E} = \frac{d_1}{E_n} + \frac{d_2 - d_1}{E_t} + \frac{h - d_2}{E_n} = \frac{h - (d_2 - d_1)}{E_n} + \frac{d_2 - d_1}{E_t}$$

where h is the depth sensitivity of the probe; $d_1$ is the distance from the surface of the tissue to a top of the inclusion; $d_2$ is the distance from the surface of the tissue to a bottom of the inclusion; $d_2 - d_1$ is a height of the inclusion; and $E_n$ and $E_t$ are the elastic moduli of normal tissue and the inclusion, respectively.

10. The device as claimed in claim 7, wherein $E_t$ is 30-200 kpa.

11. The device as claimed in claim 9, wherein $E_t$ is 30-200 kpa.

12. The device as claimed in claim 1, wherein the measuring means is configured to display a lateral size of the inclusion.

13. The device as claimed in claim 12, wherein the lateral size of the inclusion is determined by plotting the elastic moduli along a lateral axis versus a perpendicular axis, fitting the data to a Gaussian function and taking a width of the half height of the Gaussian function.

14. The device as claimed in claim 13, wherein the measuring means is configured to display two lateral sizes of the inclusion along two perpendicular axes.

15. The device as claimed in claim 1, comprising at least four said probes.

16. The device as claimed in claim 15, wherein the contact areas of said probes are sufficiently different to span a substantial portion of the range of contact area of 0.01-100 mm².

17. The device as claimed in claim 16, wherein the probes have contact areas of 16±2 mm², 42±3 mm², 67±4 mm², 96±6 mm².

* * * * *